(12) United States Patent
Matrajt et al.

(10) Patent No.: US 7,968,096 B2
(45) Date of Patent: Jun. 28, 2011

(54) **METHODS AND COMPOSITIONS FOR TREATING *TOXOPLASMA***

(75) Inventors: Mariana L. Matrajt, South Burlington, VT (US); Sergio O. Angel, Buenos Aires (AR); Pablo C. Echeverria, Buenos Aires (AR)

(73) Assignee: The University of Vermont and State Agricultural College, Burlington, VT (US)

(*) Notice: Subject to any disclaimer, the term of this patent is extended or adjusted under 35 U.S.C. 154(b) by 1034 days.

(21) Appl. No.: 11/417,673

(22) Filed: May 4, 2006

(65) Prior Publication Data

US 2006/0269618 A1  Nov. 30, 2006

Related U.S. Application Data

(60) Provisional application No. 60/677,744, filed on May 4, 2005.

(51) Int. Cl.
*A61K 39/00* (2006.01)
*A61K 30/012* (2006.01)

(52) U.S. Cl. .............................. 424/184.1; 424/273.1

(58) Field of Classification Search ............... 424/184.1
See application file for complete search history.

(56) References Cited

U.S. PATENT DOCUMENTS

| | | | |
|---|---|---|---|
| 5,284,656 A | 2/1994 | Platz et al. | |
| 5,443,791 A | 8/1995 | Cathcart et al. | |
| 5,451,569 A | 9/1995 | Wong et al. | |
| 5,708,158 A | 1/1998 | Hoey | |
| 2001/0044416 A1* | 11/2001 | McCluskie et al. | 514/44 |

OTHER PUBLICATIONS

Carme et al., Journal of Clinical Microbiology, vol. 40, No. 11, pp. 4037-4044, Nov. 2002.*
Kamal et al. (Trends in Molecular Medicine, vol. 10, No. 6, pp. 283-290, Jun. 2004).*
Fachinformation. Cisplatin 0,5 mg/ml Lösung medac. 2003:1-5. German.
Weiss LM et al., Bradyzoite development in *Toxoplasma gondii* and the hsp70 stress response. Infect Immun. Jul. 1998;66(7):3295-302.
Abuchowski A et al., Soluble polymer-enzyme adducts, in *Enzymes As Drugs*, Hocenberg and Roberts, eds., Wiley Interscience, New York, NY 1981, pp. 367-383.
Adjei A et al., Pulmonary delivery of peptide drugs: effect of particle size on bioavailability of leuprolide acetate in healthy male volunteers, *Pharm. Res.* 7(6):565-569 (1990).
Adjei A et al., Bioavailability of leuprolide following intratracheal administration to beagle dogs, *Intern. J. Pharm.* 61(1-2):135-144 (1990).
Ahn HJ et al., Molecular cloning of the 82-kDa heat shock protein (Hsp90) of *Toxoplasma gondii* associated with the entry into and growth in host cells, *Biochem. Biophys. Res. Comm.* 311:654-659 (2003).

Angel So et al., Organellar targeting and expression analysis of *Toxoplasma gondii* Hsp 90 during bradyzoite development, *Rev. Inst. Med. trop. S. Paulo*, Nov. 2003, 45(suppl.13:35-36. ISSN 0036-4665.
Bisht KB et al., Geldanamycin and 17-allylamino-17-demethoxygeldanamycin potentiate the in vitro and in vivo radiation response of cervical tumor cells via the heat shock protein 90-mediated intracellular signaling and cytotoxicity, *Cancer Res.* 63:8984-8995 (2003).
Bonne W et al., Stage-specific expression of a selectable marker in *Toxoplasma gondii* permits selective inhibition of either tachyzoites or bradyzoites. *Mol Biochem Parasitol.* Sep. 1997;88(1-2):115-26.
Boothroyd JC et al., Genetic and biochemical analysis of development in *Toxoplasma gondii*, *Philos. Trans. R. Soc. Lond. B. Biol. Sci.* 352:1347-1354 (1997).
Braquet P et al., Effect of endothelin-1 on blood pressure and bronchopulmonary system of the guinea pig, *J. Cardiovasc. Pharmacol.* 13(Suppl. 5):S143-S146 (1989).
Debs RJ et al., Lung-specific delivery of cytokines induces sustained pulmonary and systemic immunomodulation in rats, *J. Immunol.* I40(10):3482-3488 (1988).
Echeverria PC et al., *Toxoplasma gondii* Hsp90 is a potential drug target whose expression and subcellular localization are developmentally regulated. *J Mol Biol.* Jul. 22, 2005;350(4):723-34.
GenBank Database Accession No. AY344115.
Gorlich D et al., Transport between the cell nucleus and the cytoplasm, *Ann. Rev Cell Dev. Biol.* 15:607-660 (1999).
Graefe SE et al., Inhibition of Hsp90 in *Trypanosoma cruzi* induces a stress response but no stage differentiation, *Eukaryotic Cell* 1(6):936-943 (2002).
Hubbard RC et al., Anti-neutrophil-elastase defenses of the lower respiratory tract in alpha 1-antitrypsin deficiency directly augmented with an aerosol of alpha 1-antitrypsin, *Ann. Intern. Med.* 111(3):206-212 (1989).
Israelski DM et al., Toxoplasmosis in the non-AIDS immunocompromised host, *Curr. Clin. Top. Infect. Dis.* 13:322-356 (1993).
Kamal A et al., Therapeutic and diagnostic implications of Hsp90 activation, *Trends Mol. Med.* 10(6):283-290 (2004).
Kang Ki et al., In vivo functional protein-protein interaction: nuclear targeted Hsp90 shifts cytoplasmic steroid receptor mutants into the nucleus, *Proc. Nat'l. Acad. Sci.* USA 91:340-344 (1994).
Kasper LH et al., Recognition and characterization of stage-specific oocyst/sporozoite antigens of *Toxoplasma gondii* by human antisera, *J. Clin. Invest.* 75:1570-1577 (1985). Luft BJ et al., Toxoplasmic encephalitis in AIDS. *Clin Infect Dis*. Aug. 1992;15(2):211-22.
Lyons RE et al., *Toxoplasma gondii* tachyzoite-bradyzoite interconversion, *Trends Parasitol.* 18(5):198-201 (2002).
Matrajt M et al., Amino-terminal control of transgenic protein expression levels in *Toxoplasma gondii*, *Mol. Biochem. Parasitol.* 120:285-289 (2002).
Matrajt M et al., Identification and characterization of differentiation mutants in the protozoan parasite *Toxoplasma gondii*, *Mol. Microbiol.* 44(3):735-747 (2002).

(Continued)

*Primary Examiner* — Gary B. Nickol
*Assistant Examiner* — Khatol Shahnan-Shah
(74) *Attorney, Agent, or Firm* — Wolf, Greenfield & Sacks, P.C.

(57) ABSTRACT

This invention relates to a method for treatment of latent *Toxoplasma gondii* infection. The invention provides for the use of Hsp90 inhibitors for treatment of latent *Toxoplasma gondii* infection, particularly in an immunocompromised subject. Also provided is a screening method for identifying compounds useful for treating latent *Toxoplasma gondii* infection.

11 Claims, 7 Drawing Sheets

OTHER PUBLICATIONS

Nagel SD et al., The alpha- and beta-tubulins of *Toxoplasma gondii* are encoded by single copy genes containing multiple introns, *Mol. Biochem. Parasitol.* 29(2-3):261-273 (1988).

Neckers L, Effects of geldanamycin and other naturally occurring small molecule antagonists of heat shock protein 90 on HER2 protein expression, *Breast Dis.* 11:49-59 (1999).

Nemoto T et al., Mechanism of dimer formation of the 90-kDa heat-shock protein, *Eur. J. Biochem.* 233(1):1-8 (1995).

Newmark J et al., Preparation and Properties of Adducts of Streptokinase and Streptokinase-Plasmin Complex with Polyethylene Glycol and Pluronic Polyol F38, *J. Appl. Biochem.* 4:185-189 (1982).

Oeswein JQ et al., Aerosolization of proteins, *Proceedings of Symposium on Respiratory Drug Delivery II*, Keystone, Colorado (1990).

Robbins J et al., Two interdependent basic domains in nucleoplasmin nuclear targeting sequence: identification of a class of bipartite nuclear targeting sequence, *Cell* 64(3):615-623 (1991).

Rojas PA et al., Expression of a cDNA encoding a *Toxoplasma gondii* protein belonging to the heat-shock 90 family and analysis of its antigenicity, *FEMS Microbiol. Lett.* 190(2):209-213 (2000).

Sausville EA, Geldanamycin analogs, *J. Chemotherap.* 16(Suppl. 4):68-69 (2004).

Segui-Simarro JM et al., Hsp70 and Hsp90 change their expression and subcellular localization after microspore embryogenesis induction in *Brassica napus* L., *J. Struct. Biol.* 142(3):379-391 (2003).

Smith RM et al., Pulmonary deposition and clearance of aerosolized alpha-l-proteinase inhibitor administered to dogs and to sheep, *J. Clin. Invest.* 84:1145-1154 (1989).

Soete M et al., Experimental induction of bradyzoite-specific antigen expression and cyst formation by the RH strain of *Toxomplasma gondii* in vitro, *Exp. Parasitol.* 78(4):361-370 (1994).

Tomavo S et al., Characterization of bradyzoite-specific antigens of *Toxoplasma gondii*, *Infect. Immun.* 59(10):3750-3753 (1991).

Young JC et al., Hsp90: a specialized but essential protein-folding tool, *J. Cell Biol.* 154(2):267-273 (2001).

\* cited by examiner

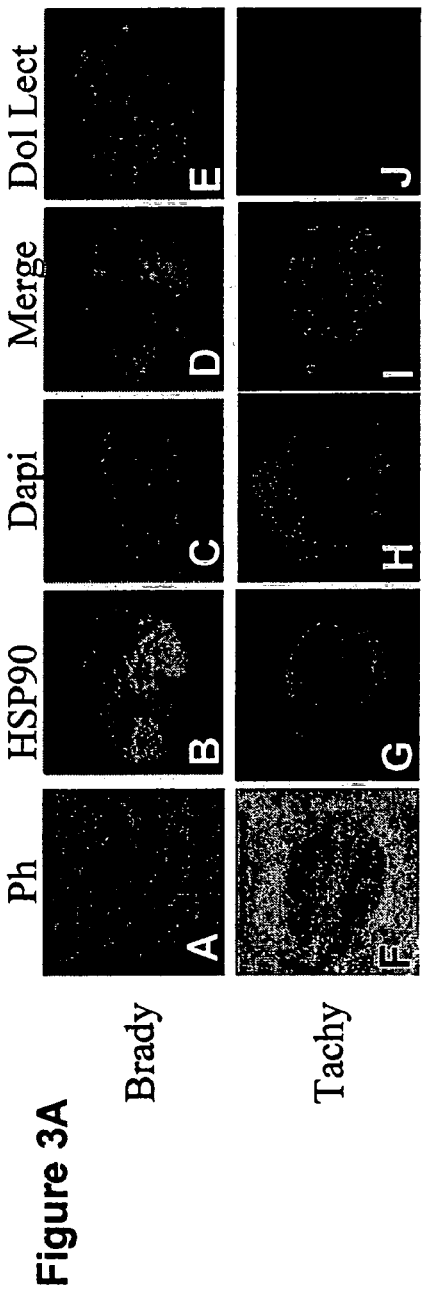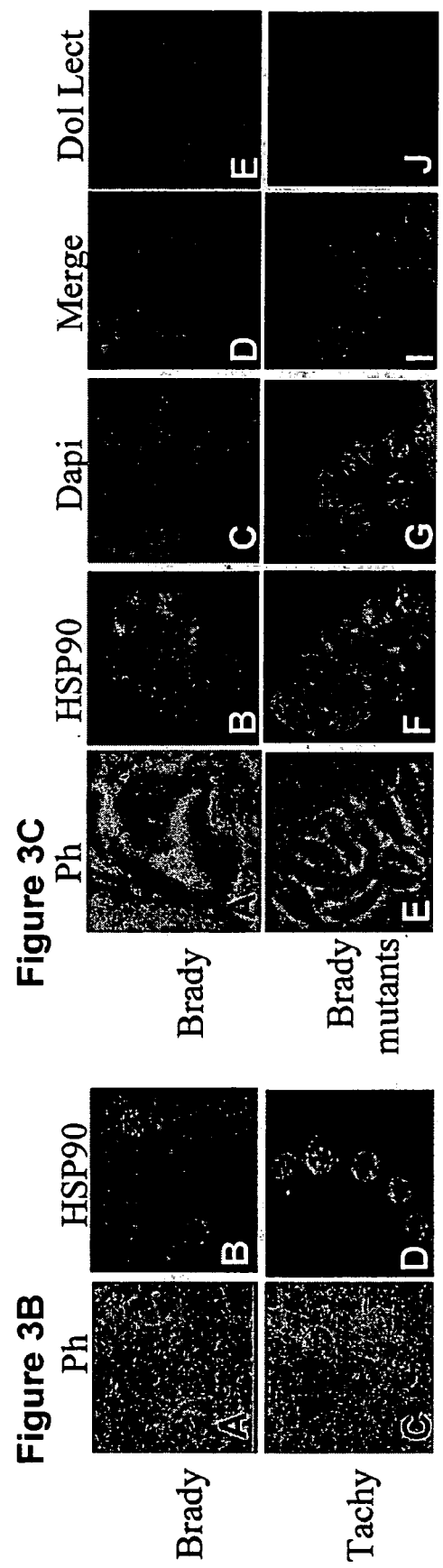
Figure 3A
Figure 3B
Figure 3C

METHODS AND COMPOSITIONS FOR TREATING *TOXOPLASMA*

RELATED APPLICATION

This application claims benefit under 35 U.S.C. 119(e) of U.S. Provisional Application No. 60/677,744, filed May 4, 2005, the entire contents of which is incorporated herein by reference.

FIELD OF THE INVENTION

This invention relates to a method for treatment of latent *Toxoplasma gondii* infection. The invention more particularly provides for the use of heat shock protein 90 (Hsp90) inhibitors in the treatment of latent *Toxoplasma gondii* infection.

BACKGROUND OF THE INVENTION

*Toxoplasma gondii* (*T. gondii*) is a ubiquitous obligate intracellular protozoan parasite that produces opportunistic infections in a large number of warm-blooded animals. This parasite can infect virtually any nucleated animal cell but usually is rapidly controlled by the cellular immune response, leaving only a latent infection that can re-emerge periodically. The asexual reproductive cycle of the parasite is characterized by two stages: rapidly growing tachyzoites and latent bradyzoite tissue cysts. Latent infection with bradyzoites is particularly important for disease propagation and causation.

*T. gondii* bradyzoites can remain as latent cysts within the tissues of an infected individual for many years. Activation of the interconversion from the bradyzoite to the tachyzoite stage can cause life-threatening opportunistic disease, particularly in immunocompromised individuals, including cancer chemotherapy patients, transplant recipients, and individuals with AIDS or other immunosuppressive disorders. Luft et al., (1988) *Clin Infect Dis* 15, 211-22); Israelski et al., (1993) *Curr Clin Top Infect Dis* 13, 322-56. These patients can develop encephalitis or other clinical manifestations due to reactivation of latent cysts, similarly to congenitally infected individuals that mainly develop brain and eye lesions.

In vitro, the induction of bradyzoite-to-tachyzoite interconversion has been associated with changes in temperature, pH, and other stress inducers known to activate expression of heat shock proteins. Morimoto et al., (1994) Cold Spring Harbor Laboratory Press, Cold Spring Harbor, N.Y.; Soete et al., (1994) *Exp Parasitol* 78, 361-370; Tomavo et al., (1991) *Infect Immun* 59, 3750-3753. Despite its clinical relevance, this conversion has been less thoroughly studied in vivo, although it has been reported that in murine models of chronic infection, subtracting interferon gamma (IFN-γ) induces bradyzoite to tachyzoite interconversion, leading to reactivation of the acute infection. Lyons, et al., (2002) *Trends Parasitol* 18, 198-201.

There currently exists no effective treatment for chronic toxoplasmosis due to a lack of drugs capable of eliminating tissue cysts.

SUMMARY OF THE INVENTION

The invention is based at least in part on the discovery by the inventors that Hsp90 expression and subcellular localization are developmentally regulated in *Toxoplasma gondii* (*T. gondii*). In particular, it has surprisingly been discovered by the inventors that *T. gondii* Hsp90 (TgHsp90) itself is involved in the interconversion between bradyzoite and tachyzoite stages of *T. gondii*, and in particular in the conversion from bradyzoite to tachyzoite stages of *T. gondii*.

The invention is also based in part on the discovery by the inventors that inhibitors of Hsp90 can be used to inhibit the interconversion between bradyzoite and tachyzoite stages of *T. gondii*, and in particular the conversion from bradyzoite to tachyzoite stages of *T. gondii*. More particularly, the invention in certain aspects relates to the discovery by the inventors that inhibitors of Hsp90 can be used to treat latent *T. gondii* infection.

In one aspect the invention is a method for treating latent *T. gondii* infection in a subject. The method according to this aspect of the invention includes the step of administering to the subject an effective amount of a heat shock protein 90 (Hsp90) inhibitor to treat the latent *T. gondii* infection. According to this aspect of the invention in one embodiment the subject otherwise does not have a condition calling for administration of the Hsp90 inhibitor. In one embodiment the subject does not have a cancer. In one embodiment the subject does not have a cancer that is sensitive to the Hsp90 inhibitor.

In one embodiment the Hsp90 inhibitor is geldanamycin A (GA), or an analog thereof, and the subject does not have a geldanamycin-sensitive cancer.

In one aspect the invention is a method for treating latent *T. gondii* infection in a subject. The method according to this aspect of the invention includes the step of administering to the subject an effective amount of a heat shock protein 90 (Hsp90) inhibitor to treat the latent *Toxoplasma gondii* infection, wherein the subject has a cancer that is not sensitive to the Hsp90 inhibitor. According to this aspect of the invention, in one embodiment the Hsp90 inhibitor is administered concurrently with a cancer therapy other than an Hsp90 inhibitor.

In one aspect the invention is a method for treating latent *T. gondii* infection in a subject. The method according to this aspect of the invention includes identifying an immunocompromised subject diagnosed with or having symptoms of *T. gondii* infection, and administering to the subject an effective amount of an Hsp90 inhibitor.

In one aspect the invention is a method for treating latent *T. gondii* infection. The method according to this aspect of the invention involves administering to a subject having cancer an effective amount of an Hsp90 inhibitor for treating latent *T. gondii* infection, wherein the subject is treated with a non-GA chemotherapeutic.

One aspect of the invention is a method for treating latent *T. gondii* infection. The method according to this aspect of the invention includes the step of administering to a subject having cancer an effective amount of an Hsp90 inhibitor for treating latent *T. gondii* infection, wherein the Hsp90 inhibitor is administered prior to a cancer therapy.

The following embodiments pertain to each of the foregoing and other aspects of the invention. In one embodiment the subject does not have a cancer sensitive to an Hsp90 inhibitor. In one embodiment the cancer therapy does not include administering an Hsp90 inhibitor to the subject. In one embodiment the subject is immunocompromised or is at risk of becoming immunocompromised. In one embodiment the subject is a subject receiving or having received immunosuppressive therapy. In one embodiment the subject is a subject receiving or having received a tissue or organ transplant. In one embodiment the subject is infected with human immunodeficiency virus (HIV).

In one embodiment the Hsp90 inhibitor is chosen from the group consisting of geldanamycin A (GA), 7-allylamino-1-deoxy-geldanamycin, 17-allylamino-17-demethoxy-geldanamycin (17-AAG), 17-dimethylaminoethylamino-geldanamycin (17DMAG), 17-(3-(4- maleimidobutyrcarboxamido)propylamino)-17-demethoxy-geldanamycin (17-GMB-APA-GA), Herbimycin A, Radicicol (RA), Novobiocin, Cisplatin, PU3, and PU24FCl.

In one embodiment the Hsp90 inhibitor is chosen from the group consisting of geldanamycin A (GA), 7-allylamino-1-deoxy-geldanamycin, 17-allylamino-17-demethoxy-geldanamycin (17-AAG), 17-dimethylaminoethylamino-geldanamycin (17DMAG), and 17-(3-(4-maleimidobutyrcarboxamido)propylamino)-17-demethoxy-geldanamycin (17-GMB-APA-GA).

In one embodiment the Hsp90 inhibitor is geldanamycin A (GA).

Another aspect of the invention is a kit including a container housing an Hsp90 inhibitor and instructions for administering the Hsp90 inhibitor to a subject according to any one of the foregoing aspects of the invention.

In a further aspect the invention is a screening method for identifying compounds for treating latent T. gondii infection. The method according to this aspect of the invention includes the steps of contacting an in vitro culture of cells infected with T. gondii with a test compound under conditions which permit stage interconversion of T. gondii; contacting an in vitro culture of cells infected with T. gondii with a reference compound under conditions which otherwise permit stage conversion of T. gondii, wherein the reference compound is an Hsp90 inhibitor; and determining the test compound is a compound for treating latent T. gondii infection when the stage interconversion of infected cells contacted with the reference compound equals or exceeds the stage interconversion of infected cells contacted with the test compound.

BRIEF DESCRIPTION OF THE DRAWINGS

FIG. 2 shows Hsp90 expression under tachyzoite growth conditions (Tachy), stress (42° C.) or bradyzoite conditions (Brady).

FIG. 3 is a series of photomicrographic images showing that the Hsp90 subcellular localization is developmentally regulated. Parasites were grown under tachyzoite conditions or bradyzoite differentiation conditions for 4 days, fixed, and immunofluorescence assays (IFA) carried out with rabbit anti-T. gondii Hsp90, TRITC-labelled D. biflorus lectin (Dol lect), or DAPI. Ph: Phase-contrast image. FIG. 3A shows immunofluorescence assay (IFA) with RH strain parasites. FIG. 3B shows phase contrast and confocal microscopy images of tachyzoites (Tachy) and bradyzoites (Brady). IFA shows Hsp90 expression. FIG. 3C shows IFA carried out with wild type bradyzoites and bradyzoite differentiation mutants.

FIG. 4 is a series of photomicrographic images showing that the Hsp90 subcellular localization is also developmentally regulated in the avirulent PK strain and during the switch from bradyzoites to tachyzoites.

FIG. 6 is two graphs showing that GA blocks tachyzoite to bradyzoite conversion. Parasites were grown under bradyzoite differentiation conditions for 4 days in the presence of 100 nM of GA or DMSO.

FIG. 7 is two graphs demonstrating that GA blocks bradyzoite to tachyzoite conversion. Released PK bradyzoites from brain cysts of infected mice were incubated with 100 nM GA or DMSO for 2 hours, washed, inoculated onto a confluent HFF monolayers, and grown under tachyzoite conditions. IFAs were performed at 4 and 24 hours post-inoculation. To identify mature bradyzoites, parasites were stained using a monoclonal anti-p21 antibody, and tachyzoites were stained using rabbit anti-SAG1.

DETAILED DESCRIPTION

Figure 1:
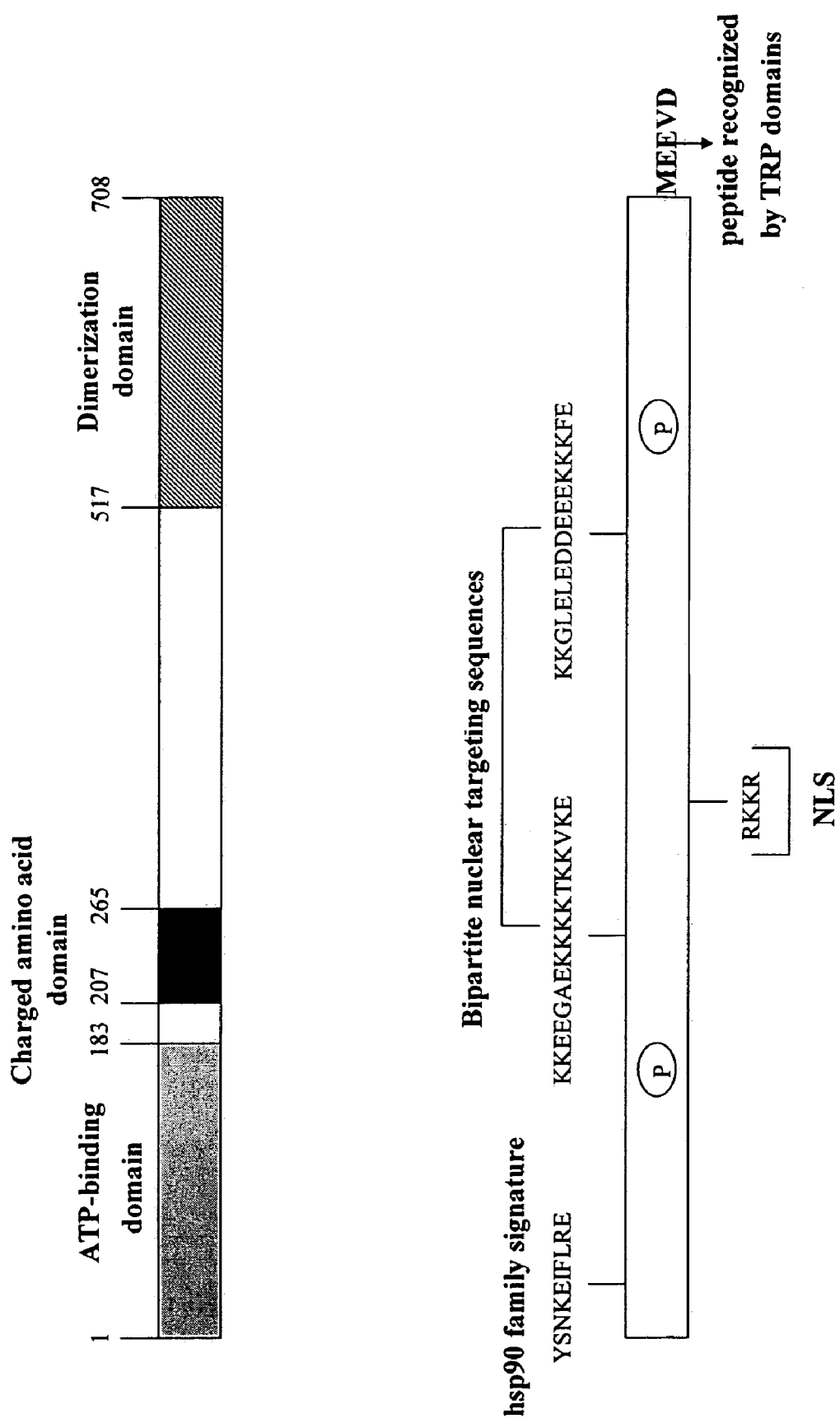
FIG. 1 is a diagram of protein sequence domains and motifs present in T. gondii Hsp90. Partial amino acid sequences shown include: YSNKEIFLRE (SEQ ID NO:5); KKEE-GAEKKKKTKKVKE (SEQ ID NO:6); KKGLELED-DEEEKKKFE (SEQ ID NO:7); MEEVD (SEQ ID NO:8); and RKKR (SEQ ID NO:9). NLS, nuclear localization signal.

The invention is based at least in part on the discovery by the inventors that Hsp90 expression and subcellular localization are developmentally regulated in *T. gondii*. In particular, it has surprisingly been discovered by the inventors that *T. gondii* Hsp90 (TgHsp90) itself is involved in the interconversion between bradyzoite and tachyzoite forms of *T. gondii*, and in particular the conversion from bradyzoite to tachyzoite forms of *T. gondii*. In addition, the inventors have discovered that inhibitors of Hsp90 can be used to inhibit these interconversions. More particularly, the invention in certain aspects relates to the discovery by the inventors that inhibitors of Hsp90 can be used to treat latent *T. gondii* infection.

Two forms of the protozoan parasite *T. gondii* are associated with intermediate hosts such as humans: rapidly growing tachyzoites responsible for acute illness, and slowly dividing encysted bradyzoites, which can remain latent within the tissues for the life of the host. An intermediate host is a host in which the *T. gondii* parasite reproduces by asexual reproduction, and can be any of a wide variety of mammals including humans. Hosts infected with *T. gondii* are said to have toxoplasmosis.

Patients with toxoplasmosis can present with a range of clinical manifestations, from subclinical lymphadenopathy to fatal, fulminant disease. In the immunocompetent host, infection with *T. gondii* may resemble infectious mononucleosis, a disease attributed to a different infectious agent, Epstein-Barr virus. The most severe forms of toxoplasmosis occur in patients who are immunocompromised. Immunocompromised hosts at risk include patients with malignancies, leukemias, collagen-vascular diseases, congenital or acquired immunodeficiency, including AIDS, organ-transplant recipients receiving immunosuppressive therapy, and other patients receiving immunosuppressive therapy. Clinical toxoplasmosis occurs in as many as 40% of patients with AIDS. Clinical toxoplasmosis usually is due to reactivation of latent *T. gondii* infection; therefore, all patients with *T. gondii* antibodies are at risk of developing active infection, with potentially fatal complications. Currently there is a need for drugs effective for treating latent *T. gondii* infection.

Drugs in current use for treatment of active toxoplasmosis include pyrimethamine, trimethoprim, sulfadiazine, clindamycin, spiramycin, chlortetracycline, azithromycin, and atovaquone, frequently used in some combination.

The term bradyzoite refers to the latent stage of *T. gondii* in an intermediate host. The slowly dividing bradyzoite can remain latent within the tissues for many years, representing a threat to immunocompromised patients. Infection is commonly acquired by ingestion of undercooked meat harboring bradyzoite tissue cysts. After passage through the gut, rupture of the cyst releases infectious parasites capable of invading across the intestinal epithelium. A bradyzoite cyst is a bradyzoite encysted in the tissue of a subject. Although bradyzoites are slow to divide, they rapidly dedifferentiate to form tachyzoites, which disseminate throughout the body and can invade across the blood-brain barrier. "Activation of latent *T. gondii* infection" is defined as the induction of bradyzoites to undergo stage interconversion and dedifferentiate into tachyzoites. Bradyzoites and tachyzoites can be found in any organ but occur most commonly in the brain, skeletal muscle, and heart muscle.

The term tachyzoite, as used herein, refers to the rapidly dividing stage of *T. gondii*. The tachyzoite stage is responsible for the acute illness associated with *T. gondii* infection and congenital defects in both humans and cattle.

Stage interconversion is defined as the process by which a bradyzoite dedifferentiates to form a tachyzoite, or the process by which a tachyzoite differentiates to form a bradyzoite.

Hsp90 is a ubiquitously expressed molecular chaperon that has been implicated in maintaining the conformation, stability, and function of key client proteins involved in signal transduction pathways related to proliferation, cell cycle progression, and apoptosis. A client protein is a cellular protein which depends on the chaperone activity of Hsp90 for its normal processing or subcellular localization. Hsp90 is also involved in processes characteristic of the malignant phenotype, including invasion, angiogenesis, and metastasis. In one embodiment Hsp90 as used herein refers specifically to *T. gondii* Hsp90. Nucleotide and amino acid sequences of *T. gondii* Hsp90 are publicly available as GenBank accession numbers AY344115 and AAQ24837, respectively, the contents of which are incorporated herein by reference.

As used herein, an Hsp90 inhibitor is an agent which interferes with or prevents the function of the molecular chaperone Hsp90. This function includes enzymatic activity and protein binding properties of Hsp90. An Hsp90 inhibitor thus interferes with or prevents enzymatic activity of Hsp90, protein binding properties of Hsp90, or both enzymatic activity and protein binding properties. Several structural motifs that are characteristic of Hsp90 proteins were found to be present in *T. gondii* Hsp90 (see FIG. 1). These include, among others: a conserved charged amino acid domain (glutamine/lysine rich); a carboxy-terminal tetratricopeptide repeat (TRP) binding site which allows the formation of multi-chaperone complexes and regulates the function of Hsp90 and Hsp70 (often a co-chaperone of Hsp90); several nuclear localization signals (NLSs); a dimerization domain; and a highly conserved N-terminal ATP-binding domain. An Hsp90 inhibitor may compete with the binding site of one of the Hsp90 client proteins. Alternatively, an Hsp90 inhibitor may bind the Hsp90 protein at a site distinct from the client protein binding site, but in doing so, it may, for example, cause a conformational change in the Hsp90 protein which is transduced to the client protein binding site, thereby precluding client protein binding. An Hsp90 inhibitor may also bind at the ATP-binding domain of Hsp90, preventing binding of ATP to Hsp90 and thereby disrupting its ability to act as a chaperone.

Hsp90 inhibitors known in the art include but are not limited to geldanamycin A (GA), geldanamycin A analogs, Herbimycin A, Radicicol, Novobiocin, and Cisplatin. In recent years several studies have focused on the role played by Hsp90 in cancer and its potential as a target of anti-cancer therapy. The drug geldanamycin A, a benzoquinone ansamycin antibiotic which has been used as a chemotherapeutic agent for use in the treatment of cancer, binds to and disrupts the function of Hsp90, and leads to the depletion of multiple oncogenic client proteins.

Geldanamycin A is a naturally occurring benzoquinone ansamycin antibiotic known in the art to specifically inhibit the chaperone protein Hsp90 by binding its N-terminal ATP-binding domain geldanamycin A is available from, among others, InvivoGen Corporation, (San Diego, Calif.).

As used herein, a geldanamycin A analog is a synthetic modified form of geldanamycin A. Several geldanamycin A analogs are known in the art, including, but not limited to, 7-allylamino-1-deoxy-geldanamycin, 17-allylamino-17-demethoxy-geldanamycin (17-AAG), 17-dimethylaminoethylamino-geldanamycin (17DMAG), and 17-(3-(4-maleimidobutyrcarboxamido)propylamino)-17-demethoxy-geldanamycin (17-GMB-APA-GA). These compounds are available from a variety of commercial sources, e.g., BIOMOL International, L.P., Plymouth Meeting, Pa.

Herbimycin A and Radicicol are also naturally occurring antibiotics that inhibit by binding to an amino terminal ATP-binding domain of Hsp90. These agents disrupt Hsp90 association with client proteins by occupying the nucleotide-binding site of Hsp90, thereby altering its conformation and preventing binding of Hsp90 with ATP and affecting the composition of Hsp90-containing multi-molecular chaperone complexes. In contrast, Novobiocin and Cisplatin are believed to bind in the C-terminal half of Hsp90. Many of the inhibitors used in the methods described herein are available from commercial sources (for example, InvivoGen, San Diego, Calif.).

The Examples illustrate the first conclusive evidence that Hsp90 expression and subcellular localization are developmentally regulated in *T. gondii*, and this protein is very likely to be involved in stage interconversion. It was discovered according to the invention that Hsp90 is present in nuclei of all mature bradyzoites obtained from the brains of infected mice, in almost all bradyzoites induced in vitro, and not present in the nuclei of bradyzoite differentiation mutants. This evidence is a very strong indication that Hsp90 plays an important role in the regulation of gene expression in these two stages. This is further supported by the fact that GA blocks conversion in both directions, suggesting this protein plays a central role in tachyzoite to bradyzoite interconversion. The majority of parasites blocked in conversion from bradyzoites to tachyzoites showed a cytosolic localization of Hsp90, suggesting the importance of the nuclear localization to the ability to differentiate.

A correlation of nuclear localization at different stages of development has been observed in *P. yoelii* and in plants, consistent with the possibility of a developmental role for Hsp90 in those species (Segui-Simarro et al., (2003) *J Struct Biol* 142, 379-391; Graefe et al., (2002) *Eukaryot Cell* 1, 936-943). For nuclear localization, a nuclear localization signal (NLS) may be involved. The receptor of these NLSs is the heterodimer importin α/β, mediating the contact to the nuclear pore complex and subsequently nuclear import itself (Gorlich et al., (1999) *Annu Rev Cell Dev Biol* 15, 607-660). Another type of NLS is the bipartite NLS (Robbins et al., (1991) *Cell* 64, 615-623). The analysis of *T. gondii* Hsp90 illustrated in the Examples revealed that it contains multiple NLS motifs including a classical type and bipartite NLS motifs (see FIG. 1). Whether all of these putative sequences are functional is not known, although during normal growth conditions effective nuclear import of Hsp90 can be obtained by addition of an extra functional NLS (Kang et al., (1994) *Proc Natl Acad Sci USA* 91, 340-344). The nuclear translocation of Hsp90 under bradyzoite conditions may be caused by the presentation of a NLS that is masked under tachyzoite conditions, and is exposed by interactions with co-chaperones or other types of regulatory proteins. Another possibility is that translocation is mediated by multiple NLS-containing client proteins.

The invention in certain aspects provides methods for treating latent *T. gondii* infection in a subject. The methods generally involve administering to the subject an effective amount of an Hsp90 inhibitor to treat the latent *T. gondii* infection.

The invention in one aspect provides a method for treating latent *T. gondii* infection by administering to a subject an effective amount of an Hsp90 inhibitor, wherein the subject does not have a geldanamycin-sensitive cancer. In one aspect of the invention a cell containing a bradyzoite cyst is contacted with an Hsp90 inhibitor in an amount effective to prevent induction of stage interconversion from bradyzoite to tachyzoite.

As used herein, the terms treat and treating refer to preventing, reducing, or eliminating at least one symptom or sign of a disease or condition in a subject. Thus for example treating a latent *T. gondii* infection in a subject refers to preventing, reducing, or eliminating at least one symptom or sign of a *T. gondii* infection in the subject. Persons of skill in the medical arts will be aware of suitable methods for assessing the status of a subject having or at risk of having a particular disease or condition.

A "subject" as used herein is any vertebrate animal including humans, non-human primates, and other mammals such as horses, cattle, swine, sheep, goats, mice, rats, cats, dogs, guinea pigs, ferrets, and rabbits. In one embodiment a subject is a human. In one embodiment a subject is a subject in need of treatment for latent *T. gondii* infection.

In one embodiment a subject is a subject that otherwise does not have a condition calling for administration of an Hsp90 inhibitor. In one embodiment a subject that otherwise does not have a condition calling for administration of an Hsp90 inhibitor is a subject without a cancer that is sensitive to geldanamycin A. In one embodiment a subject that otherwise does not have a condition calling for administration of an Hsp90 inhibitor is a subject without a cancer that is sensitive to geldanamycin A or a derivative thereof. In one embodiment a subject that otherwise does not have a condition calling for administration of an Hsp90 inhibitor is a subject without a cancer that is sensitive to the Hsp90 inhibitor. In one embodiment a subject that otherwise does not have a condition calling for administration of an Hsp90 inhibitor is a subject without a cancer. In one embodiment a subject that otherwise does not have a condition calling for administration of an Hsp90 inhibitor is a subject without an infection with an infectious organism or infectious agent other *T. gondii*.

In one embodiment a subject is a subject that is immunocompromised or a subject at risk of becoming immunocompromised. The subject may have been diagnosed as being immunocompromised as described herein or using standard medical techniques known to those of skill in the art. Alternatively a subject may exhibit one or more symptoms of *T. gondii* infection. Examples of subjects having particular susceptibility to *T. gondii* activation include but are not limited to an immunocompromised subject (arising from medical conditions or therapies), a subject receiving, having received, or about to receive chemotherapy or immunosuppressive treatment, a subject having cancer, a subject having AIDS, a subject who is HIV positive, a subject who is at risk of being HIV positive, and a subject receiving a transplant.

A subject having a latent *T. gondii* infection is a subject that has been exposed to infection by *T. gondii* and that carries bradyzoite cysts in its tissues. Such subjects may have circulating antibodies against *T. gondii*, indicating previous exposure of the subject to *T. gondii*.

In certain aspects of the invention the Hsp90 inhibitor is administered in an amount effective to treat latent *T. gondii* infection in a subject. As used herein an effective amount is an amount that is effective for producing a desired biological effect. An effective amount can mean an amount that, alone or in combination with another treatment, reduces the symptoms in a subject. In one embodiment an effective amount is an amount that reduces detectable levels of tachyzoite activation in a subject. Accordingly, in some embodiments an effective amount prevents or minimizes disease symptoms or progression associated with toxoplasmosis. An effective amount can also prevent, delay, or reduce stage interconversion of *T. gondii* from bradyzoite to tachyzoite, or reduce symptoms associated with this interconversion.

A geldanamycin-sensitive cancer is a cancerous condition that is responsive to treatment with geldanamycin A (GA) or an analog thereof. Methods for identifying a geldanamycin-sensitive cancer include contacting a cancer cell or a sample of cancer cells with GA or an analog thereof and evaluating toxicity of GA or the analog thereof, optionally when compared to a reference compound. A reference compound, as used herein, is a compound that has a known level of toxicity against the subject cells. A cancer is not geldanamycin-sensitive if contacting the cells with GA or an analog thereof results in minimal to no toxicity against the contacted cells.

In one embodiment the subject does not have a cancer sensitive to an Hsp90 inhibitor. A cancer sensitive to an Hsp90 inhibitor is a cancer or type of cancer that is not responsive to treatment with an Hsp90 inhibitor. Cancers that are not responsive to treatment with an Hsp90 inhibitor such as cisplatin are known in the art. In addition, a cancer that is not sensitive to treatment with an Hsp90 inhibitor can be identified by contacting a cancer cell or a sample of cancer cells with an Hsp90 inhibitor and evaluating toxicity of the Hsp90 inhibitor when compared to a negative control. A cancer is not sensitive to an Hsp90 inhibitor if contacting the cancer cells with an Hsp90 inhibitor results in minimal to no toxicity against the contacted cells.

In one aspect the invention provides a method for treating latent *T. gondii* infection by identifying an immunocompromised subject diagnosed with or having symptoms of *T. gondii* infection, and administering to the subject an effective amount of an Hsp90 inhibitor. An immunocompromised subject is a subject that is incapable of mounting an effective immune response. In one embodiment a subject is a subject that has not yet developed a competent immune system (e.g., a preterm neonate). An immunocompromised subject, for example, is a subject undergoing or who has undergone chemotherapy, a subject having AIDS, a subject about to receive or having already received a transplant, or a subject who is treated with immunosuppressive therapy.

In one embodiment a diagnosis of toxoplasmosis may be made by demonstrating the parasite in a tissue. In one embodiment a diagnosis of toxoplasmosis may be made by demonstrating the parasite in bronchoalveolar lavage (BAL) fluid. A diagnosis of toxoplasmosis may be confirmed by detection of anti-*T. gondii* antibodies in cerebrospinal fluid or other bodily fluid.

An immunocompromised subject diagnosed with or having symptoms of *T. gondii* infection is an immunocompromised subject exhibiting objective evidence of *T. gondii* infection. Such evidence can include cervical lymphadenopathy, fever, malaise, night sweats, myalgias, sore throat, retroperitoneal and mesenteric lymphadenopathy with abdominal pain, chorioretinitis, CNS disease, encephalitis, meningoencephalitis, mass lesions, hemiparesis, seizures, mental status changes, or visual changes. An immunocompromised subject who has AIDS can also experience brain involvement such as hemiparesis, speech abnormality, altered mental state, seizures, weakness, cranial nerve disturbances, sensory abnormalities, cerebellar signs, meningismus, movement disorders, and neuropsychiatric manifestations, or less commonly parkinsonism, focal dystonia, rubral tremor, hemichorea-hemiballismus, panhypopituitarism, diabetes insipidus, or the syndrome of inappropriate antidiuretic hormone secretion. Pulmonary disease (pneumonitis) due to toxoplasmosis can occur in AIDS patients who are not receiving appropriate anti-HIV drugs or primary prophylaxis for toxoplasmosis. Pulmonary toxoplasmosis mainly occurs in patients with advanced AIDS (mean CD4 count of less than 40 cells/mL±75 standard deviation) and primarily manifests as a prolonged febrile illness with cough and dyspnea. Eye disease, i.e., toxoplasmic chorioretinitis, can be observed in AIDS patients; it commonly manifests with ocular pain and loss of visual acuity.

In one aspect the invention provides a method for treating latent *T. gondii* infection by administering to a subject having cancer an effective amount of an Hsp90 inhibitor, wherein the subject is treated with a non-GA chemotherapeutic.

A subject having cancer is a subject that has detectable cancerous cells. A subject not having a cancer is a subject that does not have detectable cancerous cells. The cancer may be a malignant or non-malignant cancer. Cancers or tumors include but are not limited to biliary tract cancer; brain cancer including glioblastomas and medulloblastomas; bladder cancer; breast cancer; cervical cancer; choriocarcinoma; colon cancer including colorectal carcinomas; endometrial cancer; esophageal cancer; gastric cancer; head and neck cancer; hematological neoplasms including acute lymphocytic and myelogenous leukemia; AIDS-associated leukemias and adult T-cell leukemia lymphoma; intraepithelial neoplasms including Bowen's disease and Paget's disease; lymphomas including Hodgkin's disease and lymphocytic lymphomas; liver cancer; lung cancer (e.g. small cell and non-small cell); melanoma; neuroblastomas; multiple myeloma; oral cancer including squamous cell carcinoma; osteosarcomas; ovarian cancer including those arising from epithelial cells, stromal cells, germ cells and mesenchymal cells; pancreas cancer; prostate cancer; rectal cancer; sarcomas including leiomyosarcoma, rhabdomyosarcoma, liposarcoma, fibrosarcoma, synovial sarcoma and osteosarcoma; skin cancer including melanomas, Kaposi's sarcoma, basocellular cancer, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; transitional cancer and renal cancer including adenocarcinoma and Wilms tumor, as well as other carcinomas and sarcomas.

A subject treated with a non-GA chemotherapeutic is a subject that is receiving some form of chemotherapeutic agent or treatment other than treatment with GA. Chemotherapeutic treatments encompass conventional methods known to those of skill in the art, involving administration of at least one chemotherapeutic agent. Chemotherapeutic agents include but are not limited to alkylating agents, for example, nitrogen mustards, ethyleneimine compounds and alkyl sulphonates; antimetabolites, for example, folic acid, purine or pyrimidine antagonists, mitotic inhibitors, for example, vinca alkaloids and derivatives of podophyllotoxin; cytotoxic antibiotics; compounds that damage or interfere with DNA expression; and growth factor receptor antagonists; antibodies and other biological molecules known to those of ordinary skill in the art. Chemotherapeutic agents can be administered in several ways, including by mouth, intravenously, by catheter into the bladder, abdomen, chest cavity, brain, spinal cord, or liver, or by application to the skin.

Examples of non-GA chemotherapeutics include Acivicin; Aclarubicin; Acodazole Hydrochloride; Acronine; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-1a; Interferon Gamma-1b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Taxol; Taxotere; Tecogalan Sodium; Tegafur; Teloxantrone Hydrochloride; Temoporfin; Teniposide; Teroxirone; Testolactone; Thiamiprine; Thioguanine; Thiotepa; Tiazofurin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride.

Other non-GA chemotherapeutics include: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; irinotecan; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anti cancer compound; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargrarnostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene dichloride; topotecan; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer.

In one embodiment the Hsp90 inhibitor is administered to the subject concurrently with a cancer therapy. In one embodiment the cancer therapy is a cancer therapy other than an Hsp90 inhibitor. A cancer therapy other than an Hsp90 inhibitor refers to any of the non-GA chemotherapeutics listed above, as well as cancer surgery, cancer immunotherapy, radiation therapy, and any combination thereof.

In one aspect the invention provides a method for treating latent *T. gondii* infection by administering to a subject having cancer an effective amount of an Hsp90 inhibitor for treating latent *T. gondii* infection, where the Hsp90 inhibitor is administered prior to a cancer therapy.

Cancer is currently treated using a variety of modalities including surgery, immunotherapy, radiation therapy, chemotherapy, and combinations thereof. Cancer therapy as used herein specifically includes surgery, immunotherapy, radiation therapy, chemotherapy, and any combination thereof. The choice of treatment modality will depend upon the type, location and dissemination of the cancer. One of the advantages of surgery and radiation therapy is the ability to control to some extent the impact of the therapy, and thus to limit the toxicity to normal tissues in the body. Chemotherapy is frequently the most appropriate treatment for disseminated cancers such as leukemia and lymphoma as well as metastases. Chemotherapy is generally administered systemically and thus toxicity to normal tissues is a major concern.

Chronic immunosuppressive conditions can arise from radiation therapy or from pharmaceutical use such as the use of deliberate anti-inflammatories such as cox-1 or cox-2 inhibitors celecoxib (Celebrex), rofecoxib (Vioxx), naproxen (Naprosyn), non-steroidal anti-inflammatory drugs (NSAIDS) such as ibuprofen (Motrin, Advil), fenoprofen, indomethacin, and valdecoxib (Bextra), and aspirin; substance abuse such as alcoholism, intravenous drug use, morphine use; chronic infections or disease states such as gingivitis, osteomyelitis, diabetes types I and II, chronic granulomas, *Pneumocystis carinii pneumonia* (PCP) infection, recurrent fungal/yeast infections, retroviral infection, non-Hodgkin's lymphoma, Kaposi's Sarcoma, kidney failure, liver failure, malnutrition, and other conditions known to those of skill in the art.

A subject receiving a tissue or organ transplant is a subject having received or about to receive either a tissue or organ transplant during a surgical procedure. Transplants include but are not limited to whole organ, partial organ, tissue, stem cell, tissue cell, limb, and bone marrow transplants. Specific examples of tissue and organ transplants include, without limitation, kidney, heart, liver, pancreas, intestine, lung, and islet cell transplants, and any combination thereof.

A subject infected with human immunodeficiency virus (HIV) encompasses a subject who is a carrier of any of the HIV family of retroviruses or a subject who is diagnosed with active AIDS, as well as a subject having AIDS-related conditions. A carrier of HIV may be identified by any suitable method known in the art. For example, a subject can be identified as an HIV carrier on the basis that the subject is anti-HIV antibody positive, or is HIV-positive, or has symptoms of AIDS. HIV infection generally encompasses infection of a host, particularly a human host, by the human immunodeficiency virus (HIV) family of retroviruses including, but not limited to, HIV I, HIV II, HIV III (also known as HTLV-II, LAV-1, LAV-2), and the like. "HIV" can be used herein to refer to any strains, forms, subtypes and variations in the HIV family. A subject having HIV is a subject who is at any one of the several stages of HIV infection progression, which, for example, include acute primary infection syndrome (which can be asymptomatic or associated with an influenza-like illness with fevers, malaise, diarrhea and neurologic symptoms such as headache), asymptomatic infection (which is the long latent period with a gradual decline in the number of circulating CD4+ T cells), and AIDS (which is defined by more serious AIDS-defining illnesses and/or a decline in the circulating CD4 cell count to below a level that is compatible with effective immune function). In addition, it is intended to encompass subjects suspected of being infected with HIV after suspected past exposure to HIV by e.g., contact with HIV-contaminated blood, blood transfusion, exchange of body fluids, "unsafe" sex with an infected subject, accidental needle stick, receiving a tattoo or acupuncture with contaminated instruments, or transmission of the virus from a mother to a baby during pregnancy, delivery or shortly thereafter. Subjects who are HIV positive also encompass subjects who have not been diagnosed as having HIV infection but are believed to be at high risk of infection by HIV.

A subject having acquired immunodeficiency syndrome (AIDS) is a subject who exhibits more serious AIDS-defining illnesses and/or a decline in the circulating CD4 cell count to below a level that is compatible with effective immune function. A subject having AIDS also encompasses a subject having AIDS-related conditions, which means disorders and diseases incidental to or associated with AIDS or HIV infection such as AIDS-related complex (ARC), progressive generalized lymphadenopathy (PGL), anti-HIV antibody positive conditions, and HIV-positive conditions, AIDS-related neurological conditions (such as dementia or tropical spastic paraparesis), Kaposi's sarcoma, thrombocytopenia purpura and associated opportunistic infections such as *Pneumocystis*

*carinii* pneumonia, Mycobacterial tuberculosis, esophageal candidiasis, toxoplasmosis of the brain, CMV retinitis, HIV-related encephalopathy, HIV-related wasting syndrome, etc.

Actual dosage levels of the Hsp90 inhibitors of the invention may be varied so as to obtain an amount of the active component that is effective to achieve the desired therapeutic response for a particular patient and mode of administration, preferably without being toxic to the patient. The selected dosage level will depend upon a variety of factors including the activity of the particular Hsp90 inhibitor employed, the route of administration, the time of administration, the rate of excretion or metabolism of the particular agent being employed, the duration of the treatment, other drugs, agents, therapies, and/or materials used in combination with the particular Hsp90 inhibitor employed, the age, gender, weight, condition, general health and prior medical history of the patient being treated, and like factors well known in the medical arts.

A physician or veterinarian having ordinary skill in the art can readily determine and prescribe the effective amount of the Hsp90 inhibitor required. For example, the physician or veterinarian could start doses of the Hsp90 inhibitor(s) employed in the pharmaceutical composition at levels lower than that required to achieve the desired therapeutic effect and then gradually increase the dosage until the desired effect is achieved. In one embodiment the Hsp90 inhibitor is administered at a dosage level currently known in the art for use in treatment of conditions other than latent *Toxoplasma gondii* infection. Dosing may be based on results from animal model studies.

For any compound described herein the therapeutically effective amount can be initially determined from animal models. A therapeutically effective dose can also be determined from human data for Hsp90 inhibitors which have been tested in humans and for compounds which are known to exhibit similar pharmacological activities, such as other related active agents. Higher doses may be required for parenteral administration. The applied dose can be adjusted based on the relative bioavailability and potency of the administered compound. Adjusting the dose to achieve maximal efficacy based on the methods described above and other methods as are well-known in the art is well within the capabilities of the ordinarily skilled artisan.

For clinical use, the Hsp90 inhibitor may be used in combination with another agent or combination of agents useful for the treatment of toxoplasmosis. Such agents include, without limitation, pyrimethamine, trimethoprim, sulfadiazine, clindamycin, spiramycin, chlortetracycline, azithromycin, and atovaquone.

In another aspect, the present invention provides "pharmaceutically acceptable" compositions, that include a therapeutically effective amount of one or more of the Hsp90 inhibitors described herein, formulated together with one or more pharmaceutically acceptable carriers (additives) and/or diluents. The pharmaceutical compositions of the present invention may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, drops, granules, pastes for application to the tongue; parenteral administration, for example, by subcutaneous, intramuscular, intravenous or epidural injection as, for example, a sterile solution or suspension, or sustained-release formulation.

The phrase "pharmaceutically acceptable" is employed herein to refer to those Hsp90 inhibitors, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, or solvent encapsulating material, involved in carrying or transporting the subject extract from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; sterile distilled water; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

In various aspects of the invention the Hsp90 inhibitor may be administered by any means suitable to obtain the desired therapeutic effect. In one embodiment the desired effect is the prevention of stage interconversion of *T. gondii*. The Hsp90 inhibitor in this embodiment is administered in a suitable manner to reduce or prevent stage interconversion of *Toxoplasma gondii*. Administration routes include but are not limited to parenteral, oral, nasal, aerosol and enema. Parenteral administration includes but is not limited to intravenous, intramuscular, subcutaneous, intraperitoneal, and intracisternal injection or infusion techniques. Aerosol routes include but are not limited to intranasal and intrapulmonary. In one embodiment the Hsp90 inhibitor is administered orally.

For oral administration, the compounds (i.e., Hsp90 inhibitors, and other therapeutic agents) can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, i.e. EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, 1981, "Soluble Polymer-Enzyme Adducts" In: *Enzymes as Drugs*, Hocenberg and Roberts, eds., Wiley-Interscience, New York, N.Y., pp. 367-383; Newmark, et al., (1982) *J. Appl. Biochem.* 4, 185-189. Other polymers that could be used are poly-1,3-dioxolane and poly-1,3,6-tioxocane. Preferred for pharmaceutical usage, as indicated above, are polyethylene glycol moieties.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of the Hsp90 inhibitor (or derivative) or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic, e.g., powder; for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, the Hsp90 inhibitor (or derivative) may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, a-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrates include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant can be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the Hsp90 inhibitor or derivative either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

Also contemplated herein is pulmonary delivery of the Hsp90 inhibitors (or derivatives thereof). The Hsp90 inhibitor (or derivative) is delivered to the lungs of a mammal while inhaling and traverses across the lung epithelial lining to the blood stream. Other reports of inhaled molecules include Adjei et al., (1990) *Pharmaceutical Research* 7, 565-569; Adjei et al., (1990) *International Journal of Pharmaceutics* 63, 135-144 (leuprolide acetate); Braquet et al., (1989) *Journal of Cardiovascular Pharmacology* 13(suppl. 5), 143-146 (endothelin-1); Hubbard et al., (1989) *Annals of Internal Medicine* 111, 206-212 (alpha1-antitrypsin); Smith et al., (1989) *J. Clin. Invest.* 84, 1145-1146 (alpha-1-proteinase); Oswein et al., 1990, "Aerosolization of Proteins", Proceedings of Symposium on Respiratory Drug Delivery II, Keystone, Colo. (recombinant human growth hormone); Debs et al., (1988) *J. Immunol.* 140, 3482-3488 (interferon-gamma and tumor necrosis factor alpha), and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of Hsp90 inhibitor (or derivative). Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified Hsp90 inhibitor may also be prepared in different formulations depending on the type of chemical modification or the type of device employed.

Formulations suitable for use with a nebulizer, either jet or ultrasonic, will typically comprise Hsp90 inhibitor (or derivative) dissolved in water at a concentration of about 0.1 to 25 mg of biologically active Hsp90 inhibitor per mL of solution. The formulation may also include a buffer and a simple sugar (e.g., for Hsp90 inhibitor stabilization and regulation of osmotic pressure). The nebulizer formulation may also contain a surfactant, to reduce or prevent surface induced aggregation of the Hsp90 inhibitor caused by atomization of the solution in forming the aerosol.

Formulations for use with a metered-dose inhaler device will generally comprise a finely divided powder containing the Hsp90 inhibitor (or derivative) suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing Hsp90 inhibitor (or derivative) and may also include a bulking agent, such as lactose, sorbitol, sucrose, or mannitol in amounts which facilitate dispersal of the powder from the device, e.g., 50 to 90% by weight of the formulation. The Hsp90 inhibitor (or derivative) should most advantageously be prepared in particulate form with an average particle size of less than 10 µm (or microns), most preferably 0.5 to 5 µm, for most effective delivery to the distal lung.

Nasal delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, (1990) Science 249, 1527-1533, which is incorporated herein by reference.

The Hsp90 inhibitors and optionally other therapeutics may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

The pharmaceutical compositions of the invention contain an effective amount of an Hsp90 inhibitor and optionally therapeutic agents included in a pharmaceutically acceptable carrier. The term pharmaceutically acceptable carrier means one or more compatible solid or liquid filler, diluents or encapsulating substances which are suitable for administration to a human or other vertebrate animal. The term carrier denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

The therapeutic agent(s), including specifically but not limited to the Hsp90 inhibitor, may be provided in particles. Particles as used herein means nanoparticles or microparticles (or in some instances larger particles) which can consist in whole or in part of the Hsp90 inhibitor or the other therapeutic agent(s) as described herein. The particles may contain the therapeutic agent(s) in a core surrounded by a coating, including, but not limited to, an enteric coating. The therapeutic agent(s) also may be dispersed throughout the particles. The therapeutic agent(s) also may be adsorbed into the particles. The particles may be of any order release kinetics, including zero order release, first order release, second order release, delayed release, sustained release, immediate release, and any combination thereof, etc. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules which contain the Hsp90 inhibitor in a solution or in a semi-solid state. The particles may be of virtually any shape.

Both biodegradable and nonbiodegradable polymeric materials can be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels described by H. S. Sawhney, C. P. Pathak and J. A. Hubell, (1993) Macromolecules, 26, 581-587, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly (isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) may be contained in controlled release systems. The term "controlled release" is intended to refer to any drug-containing formulation in which the manner and profile of drug release from the formulation are controlled. This refers to immediate as well as non-immediate release formulations, with non-immediate release formulations including but not limited to sustained release and delayed release formulations. The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the drug there from. "Delayed release" may or may not involve gradual release of drug over an extended period of time, and thus may or may not be "sustained release."

Use of a long-term sustained release implant may be particularly suitable for treatment of chronic conditions. "Long-term" release, as used herein, means that the implant is constructed and arranged to deliver therapeutic levels of the active ingredient for at least 7 days, and in some embodiments 30-60 days. Long-term sustained release implants are well-known to those of ordinary skill in the art and include some of the release systems described above.

In various aspects of the invention the Hsp90 inhibitor is administered over a suitable period of time in order to prevent stage interconversion of *Toxoplasma gondii*. In one embodiment the Hsp90 inhibitor is administered prior to and during the course of chemotherapy treatment. In another embodiment the Hsp90 inhibitor is given on a long-term basis to a subject with a chronic illness such as HIV infection. Generally, daily doses of an Hsp90 inhibitor will be from about 0.01 milligrams/kg per day to 1000 milligrams/kg per day. It is expected that oral doses in the range of 0.5 to 50 milligrams/kg, or even 1-10 milligrams/kg per day, in one or several administrations per day, will yield the desired results. Dosage may be adjusted appropriately to achieve desired drug levels, local or systemic, depending upon the mode of administration. For example, it is expected that intravenous administration would be from an order to several orders of magnitude lower dose per day. It is expected that intravenous and other parenteral forms of administration will yield the desired results in the range of 0.1 to 10 milligrams/kg per day. In the event that the response in a subject is insufficient at such doses, even higher doses (or effective higher doses by a different, more localized delivery route) may be employed to the extent that patient tolerance permits. Multiple doses per day are contemplated to achieve appropriate systemic levels of Hsp90 inhibitors. Similarly, dosing on a less-than-daily basis is contemplated by the invention. A long-term sustained release implant may be particularly suitable for the treatment of chronic conditions. "Long-term" release, as used herein, means that the implant is constructed and arranged to deliver therapeutic levels of the active ingredient for at least 7 days, and preferably 30-60 days. Long-term sustained release implants are well-known to those of ordinary skill in the art.

In one aspect the invention provides a kit containing an Hsp90 inhibitor and instructions for administering the Hsp90 inhibitor to a subject having latent *Toxoplasa gondii* infection, including but not limited to an immunocompromised subject, a subject having cancer, or a subject with HIV infection or AIDS.

In some aspects of the invention, the kit can include a pharmaceutical preparation vial, a pharmaceutical preparation diluent vial, and Hsp90 inhibitor. The vial containing the diluent for the pharmaceutical preparation is optional. The diluent vial contains a diluent such as physiological saline for diluting what could be a concentrated solution or lyophilized powder of Hsp90 inhibitor. The instructions can include instructions for mixing a particular amount of the diluent with a particular amount of the concentrated pharmaceutical preparation, whereby a final formulation for injection or infusion is prepared. The instructions may include instructions for use in a drug delivery device. The instructions can include instructions for treating a patient with an effective amount of Hsp90 inhibitor. It also will be understood that the containers containing the preparations, whether the container is a bottle, a vial with a septum, an ampoule with a septum, an infusion bag, and the like, can contain indicia such as conventional markings which change color when the preparation has been autoclaved or otherwise sterilized.

In one aspect the invention provides a screening method for identifying compounds for treating latent *T. gondii* infection by contacting an in vitro culture of cells infected with *T. gondii* with a test compound under conditions which permit stage conversion of the parasite, contacting an in vitro culture of cells infected with *T. gondii* with a reference compound under conditions which permit stage conversion of the parasite, wherein the reference compound is a known Hsp90 inhibitor, and determining the test compound is an inhibitory compound when stage conversion of infected cells contacted with the reference compound equals or exceeds the stage conversion of infected cells contacted with the test compound. A favorable candidate Hsp90 inhibitor may subsequently be used as a reference compound in the assay.

Test compounds can include small organic molecules (molecular weight less than 1500 Daltons), nucleic acids, peptides, proteins, antibodies, polysaccharides, and lipids. Test compounds in one embodiment specifically includes derivatives of geldanamycin A.

Candidate Hsp90 inhibitors, or test compounds, may be obtained from a wide variety of sources, including libraries of natural, synthetic, or semisynthetic compounds, or any combination thereof. For example, numerous means are available for random and directed synthesis of a wide variety of organic compounds and biomolecules, including expression of randomized oligonucleotides, synthetic organic combinatorial libraries, phage display libraries of random peptides, and the like. Alternatively, libraries of natural compounds in the form of bacterial, fungal, plant and animal extracts are available or readily produced. Additionally, natural and synthetically produced libraries and compounds can be readily modified through conventional chemical, physical, and biochemical means. Further, known pharmacological agents may be subjected to directed or random chemical modifications such as acylation, alkylation, esterification, amidification, etc., to produce structural analogs of the candidate Hsp90 inhibitors.

In one embodiment the method of screening candidate Hsp90 inhibitor compounds can be performed on a large scale and with high throughput by incorporating, e.g., an array-based assay system and at least one automated or semi-automated step. For example, the assays can be set up using multiple-well plates in which cells are dispensed in individual wells and reagents are added in a systematic manner using a multiwell delivery device suited to the geometry of the multiwell plate. Manual and robotic multiwell delivery devices suitable for use in a high throughput screening assay are well known by those skilled in the art. Each well or array element can be mapped in a one-to-one manner to a particular test condition, such as the test compound. Readouts can also be performed in this multiwell array, preferably using a multiwell plate reader device or the like. Examples of such devices are well known in the art and are available through commercial sources. Sample and reagent handling can be automated to further enhance the throughput capacity of the screening assay, such that dozens, hundreds, thousands, or even millions of parallel assays can be performed in a day or in a week. Fully robotic systems are known in the art for applications such as generation and analysis of combinatorial libraries of synthetic compounds. See, for example, U.S. Pat. Nos. 5,443,791 and 5,708,158.

The present invention is further illustrated by the following Examples, which in no way should be construed as further limiting.

EXAMPLES

The results detailed in the following Examples show a strong increase in both the TgHsp90 transcript and protein levels under stress or bradyzoite differentiation conditions. To confirm a role for TgHsp90 in bradyzoite differentiation, *T. gondii* tachyzoite mutants that are defective in differentiation showed the same staining pattern as tachyzoites under differentiation conditions. In addition, Geldanamycin (GA), a benzoquinone ansamycin antibiotic capable of binding to and disrupting the function of Hsp90, blocked conversion both from the tachyzoite to bradyzoite and the bradyzoite to tachyzoite stage, suggesting an important role for this protein in the regulation of stage interconversion. These results also implicated TgHsp90 as a drug target in particular in controlling reactivation of chronic toxoplasmosis in immunocompromised individuals.

Materials and Methods

Source of the cDNA Clone, Sequencing and Sequence Analysis cDNAs with high homology to Hsp90 protein were identified in the expressed sequence tag (EST) database (http://genome.wustl.edu/est/index.php?toxoplasma=1). The cDNA described here is the clone TgESTzyd42c07.yl obtained from *T. gondii* EST project (Genome System, USA). Bluescript plasmids were excised from the Lambda ZAP® vector using the ExAssist® kit (Stratagene, La Jolla, Calif.). Plasmid DNA obtained from the positive clones was sequenced using a Perkin Elmer ABI 377 machine and the BigDye® Terminator Cycle Sequencing Kit (Perkin-Elmer, Boston, Mass.). Nucleotide sequence data of *T. gondii* Hsp90 is available in the GenBank™ database under the accession number AY344115.

Database searches, sequence comparisons and domain analysis were performed using Blastn, Blastx, Blast 2 and Blast domain programs (http://www.ncbi.nlm.nih.gov/Blast and http://www.toxoDB.org). BCM search launcher programs (http://searchlauncher.bcm.tmc.edu) were used to obtain putative open reading frames. PSORT (http://psort.nibb.ac.jp/) was used to find putative domains.

Parasite In Vitro Differentiation and Manipulation

RH UPRT knock-out parasites can be induced to differentiate into bradyzoites in low $CO_2$, resulting in pyrimidine starvation. (Bohne et al., (eds) (1997) Stage-specific expression of a selectable marker in *T. gondii* permits selective inhibition of either tachyzoites or bradyzoites Vol. 88. *Mol Biochem Parasitol*; Bohne et al., (1997) *Mol Biochem Parasitol* 88, 115-126). $CO_2$ depletion was accomplished by inoculating tachyzoites with low inocula (parasite/host cell ratio<1:10) into a human foreskin fibroblast (HFF) host cell monolayer in minimal essential medium (Dulbecco's modified Eagle's medium (DMEM)) with 10% FBS (Gibco® Cell Culture Products, Invitrogen, Carlsbad, Calif.) without $NaHCO_3$ but containing 25 mm HEPES. Cultures were equilibrated at pH 7 and incubated at 37° C. at ambient $CO_2$ (0.03%). In other experiments, geldanamycin A (GA) (100 nM) or DMSO (as a control) were added to the same media and conditions. By about 4 days, the vacuoles showed distinct signs of becoming cysts: parasite division was reduced and cyst wall was evident (Bohne et al., (eds) (1997) Stage-specific expression of a selectable marker in *Toxoplasma gondii* permits selective inhibition of either tachyzoites or bradyzoites Vol. 88. *Mol Biochem Parasitol*; Bohne et al., (1997) *Mol Biochem Parasitol* 88, 115-126). Bradyzoite induction under this method was assessed and followed by cyst wall detection using the *Dolichos biflorus* lectin (Boothroyd et al., (1997) *Philos Trans R Soc Lond B Biol Sci* 352, 1347-1354).

To induce PK tachyzoites, a clone isolated from cystogenic *T. gondii* Me49 strain (Kasper et al., (1985) *J Clin Invest* 75, 1570-1577), to differentiate to bradyzoites in vitro, the high-pH method was chosen (Soete et al., (1994) *Exp Parasitol* 78, 361-370). A confluent monolayer of HFF was infected with approximately $2 \times 10^5$ tachyzoites in each well of a 24-well plate or $10 \times 10^6$ in 8 cm diameter tissue culture petri dish and were grown in standard tachyzoite conditions for 4 h at pH 7.2, under 5% $CO_2$ to permit invasion and initial growth. After this, the medium was removed and replaced with inducing medium (RPMI/HEPES, pH 8.1, 5% fetal bovine serum) and the culture placed in a 37° C. incubator (at ambient $CO_2$ 0.03%). In other experiments, GA (100 nM) or DMSO (as a control) were added to the same media and conditions. The inducing medium was replaced every 2nd day. By about 2 days, the vacuoles showed distinct signs of becoming cysts (rounding up and showing packed parasites, compared with the flattened rosettes of the tachyzoite vacuoles) and parasite division rate was reduced. Antibodies specific to the tachyzoite surface protein SAG1 (murine mAb α-p30 T4IE5, obtained from J F Dubremetz, Université de Montpellier II) or to the bradyzoite specific protein P34 murine mAb α-34 T82C2) or P21 (murine mAb T84G10) (Tomavo et al., (1991) Infect Immun 59, 3750-3753), as well as *D. biflorus* lectin (Sigma, St Louis, Mo.), were used to control bradyzoite development.

In both models, for bradyzoite isolation, bradyzoite induction medium was removed, cells were washed once with PBS, the monolayer was scraped and passed five times through a 27-gauge needle, followed by once through a 30-gauge needle to release parasites from the host cells. The parasites were then centrifuged at 1800 r.p.m. for 10 min at room temperature and resuspended in sterile PBS and counted in a Neubauer improved chamber. Tachyzoite cultures were obtained from growing parasites in standard tachyzoite conditions and processed similarly except that release from the HFFs used only a 27-gauge needle. Both stages of parasites were purified from the host cell material by passage through a 3 μm-pore size filter (Nucleopore Corporation, Pleasanton, Calif.).

Reverse Transcriptase-Polymerase Chain Reaction (RT-PCR) Assays

One μg of purified total RNA from either tachyzoites or bradyzoites was reverse transcribed at 42° C. in a buffer containing 1 mM of corresponding reverse primer, 2 mM of dNTP and 25 U of AMV reverse transcriptase (Promega, Madison, Wis.). The reaction mixture was heat inactivated at 70° C. for 15 min. PCR amplifications were performed with tenfold serial dilutions of these cDNAs produced using 2.5 U of Taq DNA polymerase (Promega) in 50 μl reaction volumes containing 10 mM Tris-HCl (pH 9.0), 50 mM KCl, 0.1% Triton X-100, 1.5 mM $MgCl_2$, 200 mM of dNTP and 100 pM of each primer. Thermal cycling conditions were: (1) denaturation at 94° C. for 1 min; (2) annealing at 55-65° C. (depending upon each pair primer); (3) elongation at 72° C. for 2 min; (4) at the end, an additional extension was done at 72° C. for 10 min. To ensure that equal amounts of cDNA from each parasitic stage were being compared, the primers derived from *T. gondii* α-tubulin genes (Nagel et al., (1988) *Mol Biochem Parasitol* 29, 261-273), 5'-CGACG-GTGGGGTCCAAAT-3' (SEQ ID NO:1) and 5'-GAGCTCT-TCTGCCTGGAA-3' (SEQ ID NO:2) were used as control.

The pair primers specific for *T. gondii* Hsp90 (Rojas et al., (2000) *FEMS Microbiol Lett* 190, 209-213) were 5'-TTGGT-CACTTCCGAGTAC-3' (SEQ ID NO:3) and 5'-ATCTTC-CTCGGCGCGGCAA-3' (SEQ ID NO:4). PCR products were electrophoresed on agarose gels, stained with ethidium bromide, scanned and quantified using a computer program (Scion Image for Windows) for a semi-quantitative RT-PCR analysis. Data are expressed as mean relative density of Hsp90 amplicon with respect to α-tubulin for each dilution.

Immunoblot Analysis

Protein extracts from parasites that were grown under tachyzoite, stress and bradyzoite conditions were analyzed. Protein extracts from uninfected human foreskin fibroblasts (HFF) were also assayed. All extracts were performed in sodium dodecyl sulfate (SDS)-polyacrylamide gel electrophoresis (SDS-PAGE) sample buffer (Rojas et al., (2000) *FEMS Microbiol Lett* 190, 209-213). Equal numbers of parasites (determined by counting extracellular organisms in a hemocytometer) were loaded onto SDS-PAGE 10% gels, electrophoresed, and transferred to nitrocellulose membrane as previously described (Rojas et al., (2000) *FEMS Microbiol Lett* 190, 209-213). Non-specific binding sites were blocked with 5% non-fat dried milk in PBS containing 0.05% Tween-20 (PBS-T) and the membranes were then incubated (1 hour, room temperature) with the rabbit anti-*T. gondii* Hsp90 polyclonal antibody diluted 1:500. The membranes were washed with PBS-T prior to incubation with horseradish peroxidase-conjugated anti-rabbit secondary antibodies, diluted 1:1000 (Santa Cruz Biotechnology, Santa Cruz, Calif.). Immunoreactive protein bands were visualized by enhanced chemiluminiscence detection (ECL Plus™ System, Amersham Biosciences, Piscataway, N.J.) and with 5-bromo-4-chloro-3-indolyl phosphate/nitro blue tetrazolium (BCIP/NBT) liquid substrate system (Sigma). Results were analyzed by densitometry. Coomassie blue staining of a duplicate SDS-PAGE gel confirmed equal loading of each lane.

Immunofluorescence Localization of Hsp90 Protein

Tachyzoites were inoculated into host cell monolayers (HFF) and grown under tachyzoite conditions for 24 h or shifted to bradyzoite differentiation conditions for 4 days. Cells were washed twice with PBS then fixed and permeabilized with 4% formaldehyde and 0.1% Triton X-100 in PBS for 10 min. After washing with PBS, cells were blocked with 1% bovine serum albumin and incubated with the appropriate dilution of each primary antibody for 1 hour using rabbit anti-*T. gondii* Hsp90 serum, mouse anti-P30 (α-SAG1), or anti-P34 serum (α-p34, mAb T82C2). Tomavo et al., (1991) *Infect Immun* 59, 3750-3753. Following incubation, cells were washed three times with PBS and then incubated with the corresponding secondary antibodies (1:200) using fluorescein isothiocyanate (FITC)-conjugated goat anti-rabbit (green color), rhodamine isothiocyanate (TRITC)-conjugated goat anti-rabbit (red color) (Jackson ImmunoResearch Laboratories, Inc., West Grove, Pa.) and/or (TRITC)-labelled *D. biflorus* lectin. Coverslips were washed three times and mounted in Fluoromount mounting medium with DAPI (Molecular Probes, Eugene, Oreg.) and viewed using a Zeiss® Axiovert® 35 inverted microscope equipped with a 100 W Hg-vapor lamp and epifluorescence filter sets. The DAPI staining reveals the location of the nucleus (blue color) and *D. biflorus* lectin the presence of parasite cyst wall. Green, red, and blue fluorescence were recorded separately, and the images were merged using Adobe® Photoshop®.

In Vitro Transformation of Encysted Bradyzoites into Tachyzoites

Cysts were isolated from brains of mice infected intraperitoneally 4 weeks before with PK or Me49 strain tachyzoites. Cysts were purified by isopycnic centrifugation on a percoll gradient and encysted bradyzoites were freed by trypsin digestion. In the case of GA experiments, free bradyzoites were incubated in culture media with GA 500 nM or DMSO for 2 h, then parasites were pelleted and washed. One hundred thousand bradyzoites were inoculated onto 12 mm coverslips covered with a confluent monolayer of HFFs. Intracellular localization of Hsp90 was followed by IFA after 4 and 24 hours of infection using anti-Hsp90 serum (1:100). Monoclonal antibodies, specific to the tachyzoite surface protein SAG1 or to the bradyzoite specific protein P21 (mAb T84G10), were used to monitor stage conversion.

Effect of Geldanamycin A (GA) on Stage Conversion and Intracellular Localization of Hsp90

GA (InvivoGen, San Diego, Calif.) was dissolved in dimethyl sulfoxide (DMSO) at 1000 mg/ml. The drug was diluted in normal culture media to the required concentrations prior to use. A range of concentrations from 1 nM to 5 µM were initially assayed to determine an effective concentration for subsequent experiments. DMSO was added in similar concentrations to control slides. For replication rate studies, the number of parasites per parasitophorous vacuole or cysts (PV-Cyst) was determined for at least 100 PV-Cyst per treatment (GA or DMSO) in replicate experiments. To measure the effect of GA on stage conversion, GA was added in bradyzoite induction experiments (as described above), slides were analyzed by IFA, and the number of P34 positive vacuoles was determined in both GA and DMSO treated cultures. Analysis of intracellular localization of Hsp90 was assessed in the same way but using rabbit anti-TgHsp90 serum. In the in vitro transformation of encysted bradyzoites into tachyzoites experiments, parasites were treated with GA (as described above) and then analyzed by IFA counting P21 and P34 positive PV-Cysts in treated and control groups. For replication rate studies, the number of parasites per PV/cysts was determined for at least 100 PV-Cyst per treatment in replicate experiments.

Example 1

Protein Sequence Analysis of *T. gondii* Hsp90

One of the *T. gondii* ESTs showing high identity with Hsp90 sequences (TgESTzyd42c07.yl) was sequenced. The *T. gondii* Hsp90 is a 2933-bp cDNA encoding a predicted 708 amino acid protein with a theoretical mass of 81.9 kDa. The deduced amino acid sequence showed 100% identity with the Hsp90 previously described (Ahn et al., (2003) *Biochem Biophys Res Commun* 311, 654-659). Several structural motifs that are characteristic of Hsp90 proteins were also present in *T. gondii* Hsp90 (FIG. 1). These included the ATP-binding domain which is related to a superfamily of homodimeric ATPases comprising, in addition to Hsp90, DNA gyrase and Histidine kinase proteins. This highly conserved N-terminal domain is also the binding site for GA. PROSITE database analysis revealed that this protein contained several signature features of Hsp90 proteins including a conserved charged amino acid domain (glutamine/lysine rich), a tetratricopeptide repeat (TRP) binding site (peptide sequence MEEVD (SEQ ID NO:8) at its carboxyl terminus which allows the formation of multi-chaperones complexes and regulates the function of Hsp90 and Hsp70 (Young et al., (2001) *J Cell Biol* 154, 267-273). A dimerization domain with similarity to the human Hsp90 (Nemoto et al., (1995) *Eur J Biochem* 233, 1-8)

was also identified. In addition, a classical nuclear localization signal (NLS) and two bipartite NLSs were detected.

Example 2

Figure 2A:
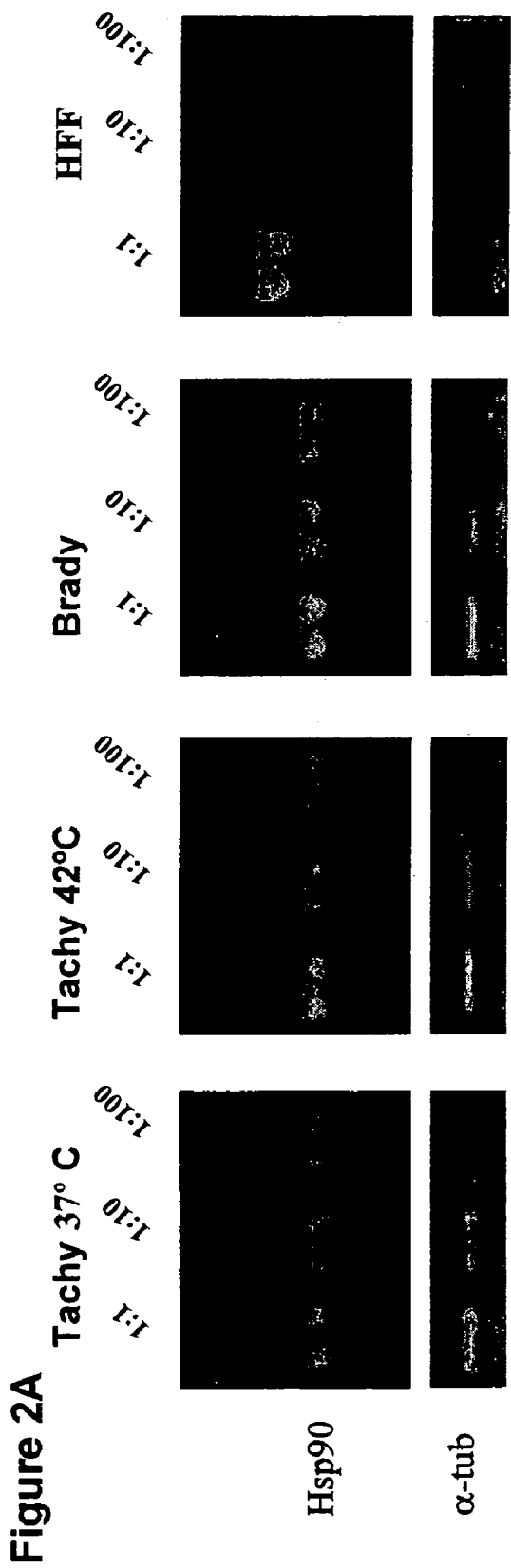
FIG. 2A is a series of four gels showing the results of semi-quantitative RT-PCRs performed with tenfold serial dilutions of tachyzoite, stressed tachyzoite and bradyzoite cDNAs. The housekeeping gene α-tubulin (α-tub) was used as control. Protein extracts from uninfected human foreskin fibroblasts (HFF) cells were also assayed.
Figure 2C:
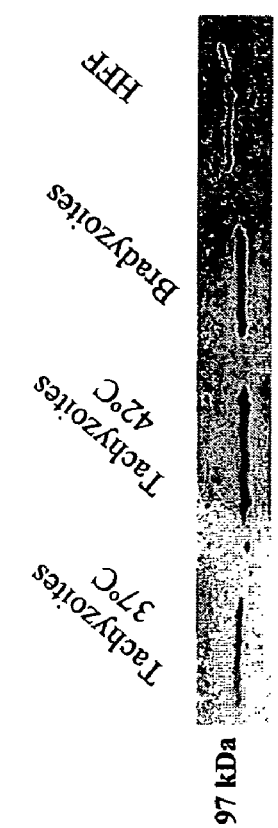
FIG. 2C shows a western blot with rabbit anti-T. gondii Hsp90 polyclonal antibody. Protein extracts from uninfected HFF cells were also assayed.
Figure 2B:
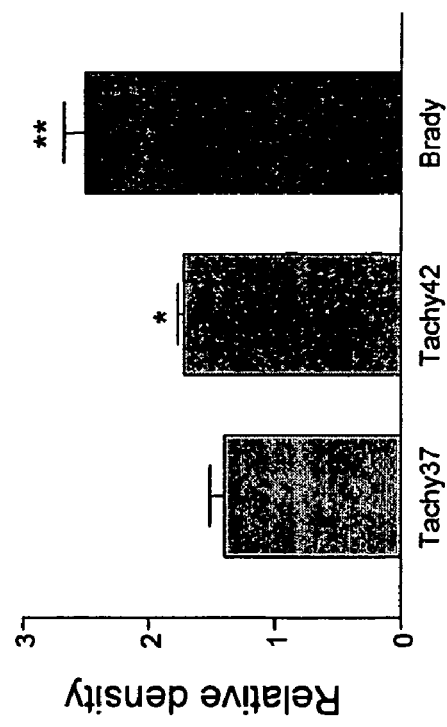
FIG. 2B is a graph showing the results of scanning and quantifying the RT-PCR gels using a computer program (htpp//rsb.info.nih.gov:nih-image/). Data are expressed as mean relative density (y-axis) of Hsp90 amplicon with respect to α-tubulin. The significance of data was determined by Student's t-test. * and **, significantly different (P<0.05 and P<0.01, respectively) from the Tachy 37° C. group.

Induction of Hsp90 Expression Under Heat Stress and Bradyzoite Differentiation Conditions To analyze the Hsp90 expression during heat stress and tachyzoite-bradyzoite conversion, RH ΔUPRT strain parasites were grown under tachyzoite conditions, heat stress (1 hour, 42° C.), or bradyzoite differentiation conditions ($CO_2$ starvation) (Bohne et al., (1997) Mol Biochem Parasitol 88, 115-126). The development of bradyzoites was monitored utilizing a D. biflorus lectin-based immunofluorescence assay (Boothroyd et al., (1997) Philos Trans R Soc Lond B Biol Sci 352, 1347-1354). The transcription profile was examined using semi-quantitative RT-PCR (FIG. 2A). To ensure that equal amounts of cDNA from each parasitic stage were being compared, mRNA from the housekeeping gene α-tubulin was also assayed in parallel. A 24% induction of Hsp90 expression was observed in stressed tachyzoites compared to unstressed parasites (FIG. 2A and FIG. 2B). Under bradyzoite conditions, however, an 80% increase in Hsp90 mRNA levels was observed (FIG. 2A and FIG. 2B).

In order to determine if the changes in mRNA levels corresponded to differences at the protein level, protein expression was assayed by western blot using a rabbit anti-T. gondii Hsp90 antibody. FIG. 2C shows that Hsp90 was induced following 1 hour of heat shock (42° C.) or under bradyzoite differentiation conditions: a sixfold and fivefold increase in Hsp90 expression was estimated by densitometry, respectively. Similar results were obtained with the avirulent PK strain and using a different method to induce bradyzoite formation (alkaline stress).

Example 3

Stage-Specific Subcellular Localization of Hsp90

In order to determine the subcellular localization of Hsp90 during bradyzoite formation, immunofluorescence assays (IFA) were carried out under tachyzoite conditions or parasites cultivated for 4 days under bradyzoite differentiation conditions, with an antibody toward the T. gondii Hsp90 (green pseudocolor in FIG. 3A). The Hsp90 was present in the cytosol and excluded from the nucleus in tachyzoites (FIG. 3A, panels G and I). In contrast, bradyzoites exhibited a dramatic change in Hsp90 localization, showing a cytoplasmic and nuclear staining pattern (FIG. 3A, panels B and D). These results were confirmed by confocal microscopy: the Hsp90 was excluded from the nucleus in all tachyzoite sections (FIG. 3B, one section shown) and present in the nucleus and cytosol of all bradyzoite sections (FIG. 3B, one section shown).

To examine whether the change in the subcellular localization is a general response to stress or $CO_2$ starvation conditions rather than a response to bradyzoite formation per se, the Hsp90 localization in a bradyzoite differentiation mutant was analyzed. The results demonstrated a global defect of bradyzoite gene induction and other aspects of differentiation. FIG. 3C shows the Hsp90 staining pattern of wild type parasites and the bradyzoite differentiation mutant B7 grown under differentiation conditions for 4 days. The mutant exhibited the same staining pattern as wild type tachyzoites, suggesting a strong correlation between the subcellular localization of Hsp90 and these two developmental stages.

Figure 4A:
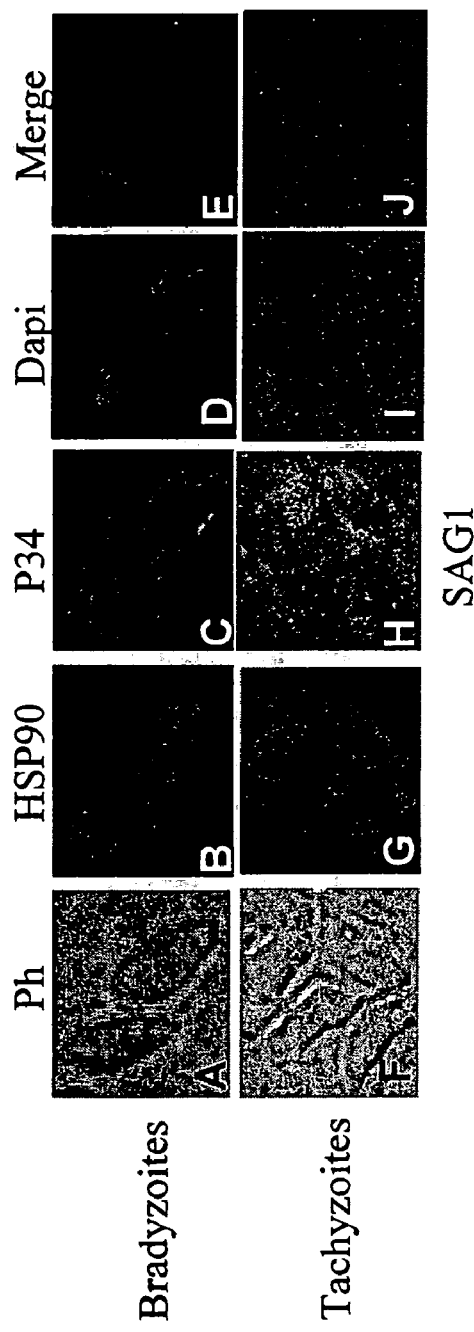
FIG. 4A shows parasites grown under tachyzoite conditions or bradyzoite differentiation conditions for 4 days (alkaline stress: culture media at pH 8.1). To control for bradyzoite development in the cultures, an anti-SAG1 monoclonal antibody, specific to the tachyzoite stage, or an anti-P34, specific to the bradyzoite stage, were used. Ph: Phase-contrast image.

To extend and confirm the in vitro results obtained with RH strain parasites, similar studies were carried out with the avirulent PK strain that is able to form cysts in mice. Also, an additional method, alkaline stress, was utilized for in vitro bradyzoite formation. FIG. 4A shows the staining pattern obtained with the PK strain under tachyzoite conditions or 4 days of bradyzoite induction under alkaline stress. Comparable results between RH and PK strain were obtained, indicating the change in the subcellular localization is not restricted to RH strain or $CO_2$ starvation conditions. Of note, some PK bradyzoites showed an Hsp90 staining similar to tachyzoites, suggesting that at early stages of differentiation a mixed population of tachyzoites and bradyzoites may be present.

Figure 4B:
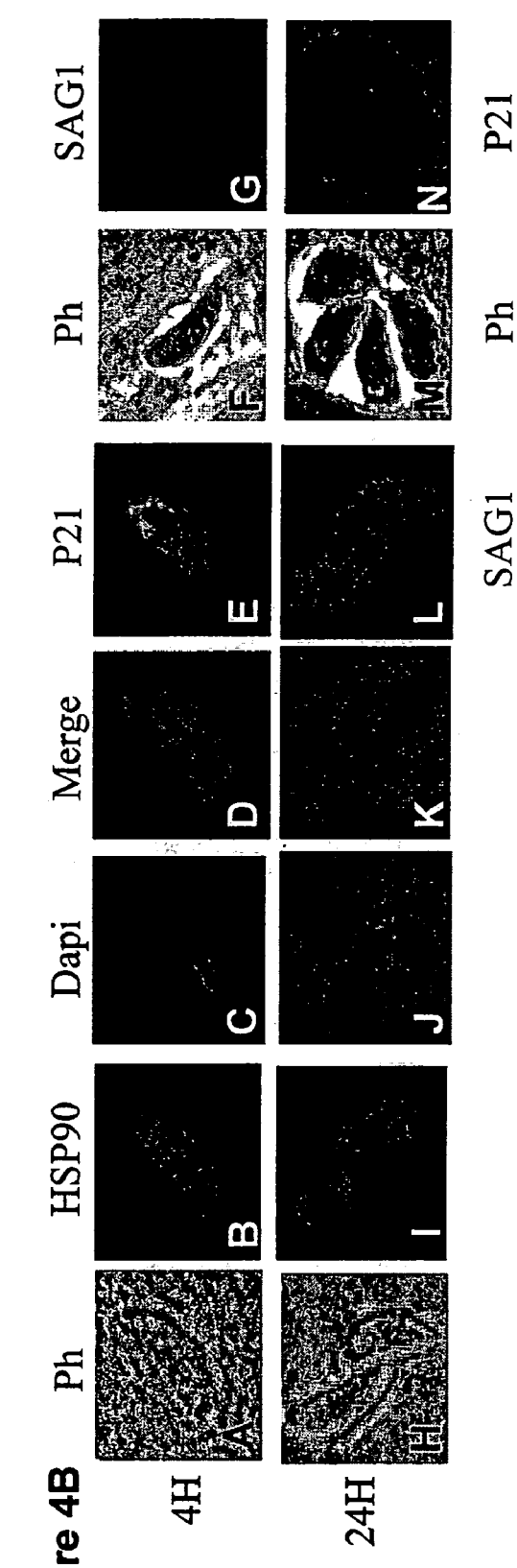
In FIG. 4B, released PK bradyzoites from brain cysts of infected mice were inoculated onto a confluent HFF monolayer under tachyzoite growth conditions and IFAs carried out at 4 or 24 hours post-inoculation. Anti-p21 monoclonal antibody was used to control for mature bradyzoites.

To examine the Hsp90 localization during bradyzoite to tachyzoite conversion, freshly released PK bradyzoites obtained from brain cysts of experimentally infected mice were inoculated into host cell monolayers under tachyzoite growth conditions, and IFAs were performed 4 or 24 hours post-inoculation into the host monolayers (FIG. 4B). Four hours post-inoculation, the parasites showed a bradyzoite staining pattern for the Hsp90 and this pattern correlated with the expression of the bradyzoite specific protein P21 (a marker that has been correlated with mature cysts) but not the tachyzoite specific marker SAG1. Twenty-four hours post-inoculation, several parasites showed a tachyzoite Hsp90 staining, and the same parasites were P21 negatives and SAG1 positives, and showed the first round of cell division. Similar results were obtained using Me49 strain which is a more efficient cyst former.

Taken together, these data strongly indicated that the subcellular localization of Hsp90 is stage-specific.

Example 4

Figure 5:
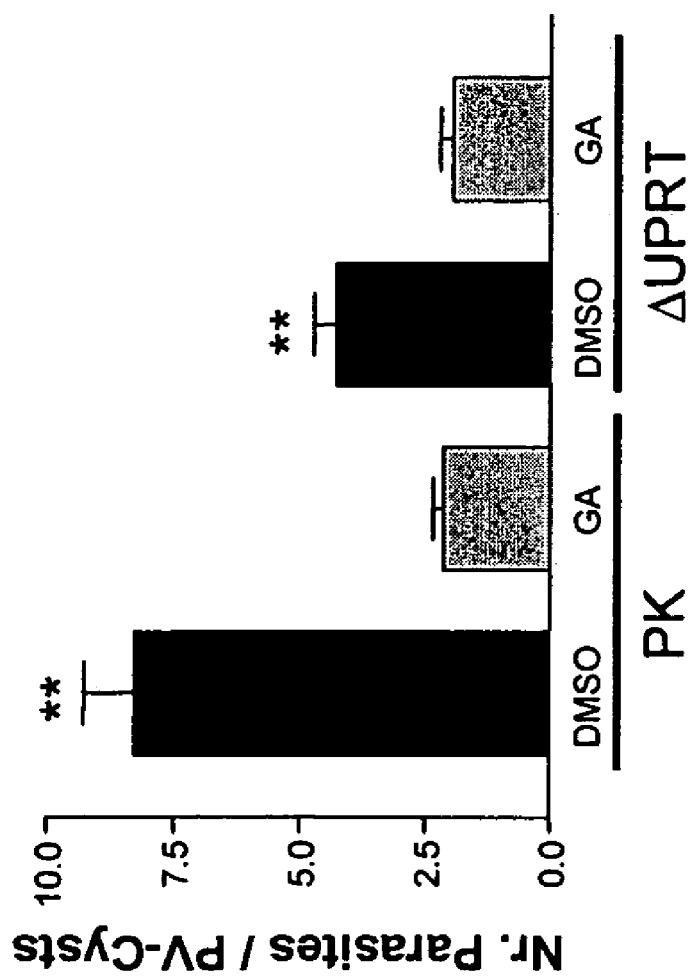
FIG. 5 is a graph showing that geldanamycin A (GA) affects bradyzoite replication rate. PK strain (an avirulent derivative of the Me49 strain) and ΔUPRT strain (a strain with a stage-specific selectable marker) parasites were grown under bradyzoite differentiation conditions for 4 days in the presence of 100 nM of GA or DMSO. IFAs were carried out with rabbit anti-T. gondii Hsp90 serum. Fluorescent parasites were counted and the number of parasites per parasitophorous vacuole (PV)-cysts was graphed. One hundred PV-cysts were counted. Student t test was performed by Prism3™ program (Graphpad). *p 0.05, **p 0.01. The y-axis represents the number of parasites/PV-cysts.

GA Blocks Both Tachyzoite to Bradyzoite and Bradyzoite to Tachyzoite Interconversion To determine the effect of GA on parasite growth under bradyzoite conditions, parasites from RH and PK strains were cultivated for 4 days in the presence of 100 nM GA (FIG. 5). A significant reduction of parasite growth (~3 fold in PK and ~2 fold in RH) in GA treated cultures was observed compared to DMSO controls. In addition, a lower number of infected cells was observed in the presence of GA in the culture media. Both the growth rate and the entry of tachyzoites to the host cells is reduced in the presence of GA (Ahn et al., (2003) Biochem Biophys Res Commun 311, 654-659).

Figure 6A:
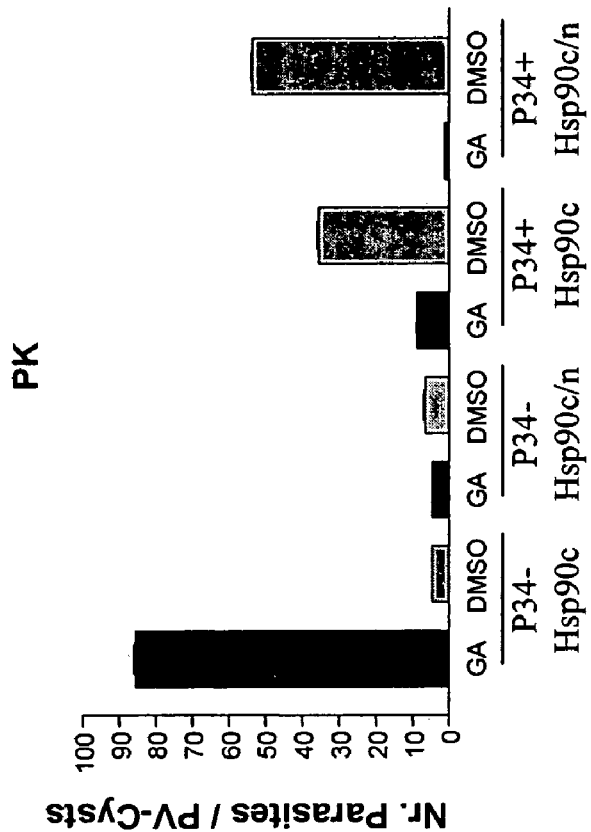
FIG. 6A is RH UPRT knock-out parasites.
Figure 6B:
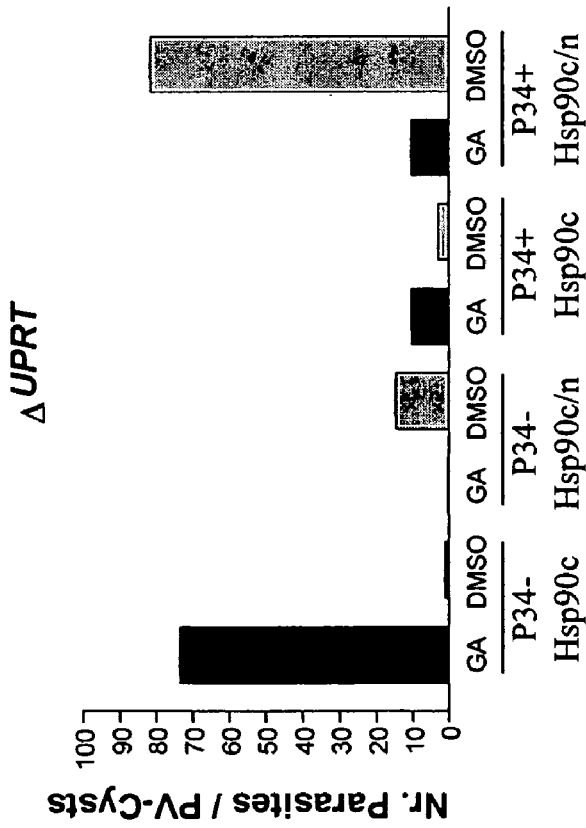
FIG. 6B is PK parasites. The y-axes depict the number of parasites/PV cysts. Cytoplasmic (c) and nuclear (n) Hsp90 localization was determined by IFA with rabbit anti-T. gondii Hsp90 serum. Parasites were also stained with the bradyzoite-specific marker p34 and scored as P34 positive (p34+) or negative (p34−). The number of P34−/Hsp90c; P34−/Hsp90c,n; P34+/Hsp90c; and P34+/Hsp90c,n per 100 PV-Cysts was counted at random, in three independent experiments.

To examine the effect of GA on tachyzoite to bradyzoite conversion, the subcellular localization of Hsp90 was analyzed. FIG. 6 shows the staining pattern for Hsp90 and the bradyzoite specific marker p34 (Soete et al., (1994) Exp Parasitol 78, 361-370) of parasites cultivated for 4 days under bradyzoite conditions with or without GA. The parasite population was classified in four categories: P34 negative (P34−) parasites (tachyzoites), with an extranuclear-only cytoplasmic Hsp90 (Hsp90c; i.e. tachyzoite staining) or cytoplasmic and nuclear Hsp90 (Hsp90c,n; i.e. bradyzoite staining), P34+ parasites (bradyzoites) with Hsp90c or Hsp90c,n localization (FIG. 6). Treatment with GA drastically reduced bradyzoite formation: about 75% of parasite vacuoles showed P34− and Hsp90c in the GA treated cultures (tachyzoite phenotype) and more than 75% showed P34+ and Hsp90n,c in the DMSO controls (bradyzoite phenotype); see first and last bar on RH ΔUPRT strain (FIG. 6). Similar results were obtained with PK strain (FIG. 6). Of note, a greater number of parasite vacuoles showing a P34+, Hsp90c staining pattern was observed, suggesting the presence of a mixed population of tachyziotes and bradyzoites after 4 days of induction when switching this strain in vitro. Similar results were obtained when *D. biflorus* lectin was used as a bradyzoite marker, and similar results were obtained in multiple experiments, highlighting a feature of PK strain under $CO_2$ starvation conditions.

In addition, fresh extracellular (i.e., separated from host cells) tachyzoites were treated for 2 hours with GA, washed to eliminate the drug, and inoculated onto host cell monolayers under bradyzoite conditions. A decreased level of invasion was observed, but the parasites that invaded successfully replicated at a similar rate compared to the wild type and developed into bradyzoites, suggesting a reversible effect of GA on tachyzoites.

Figure 7A:
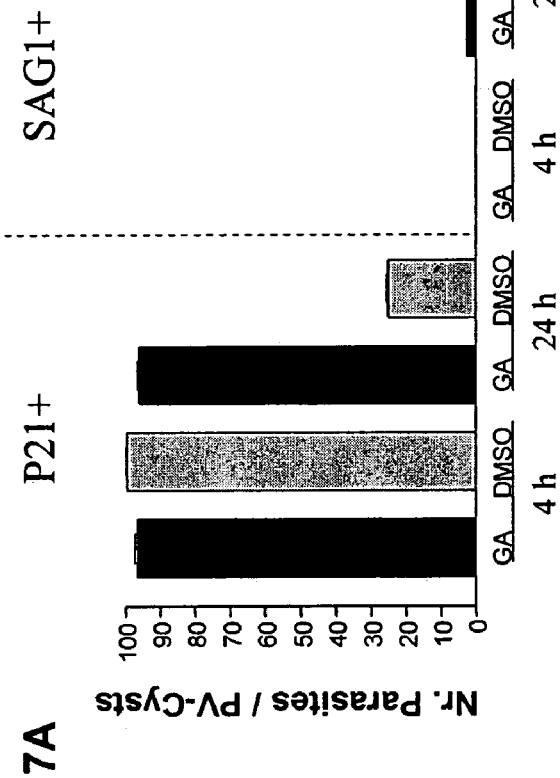
As shown in FIG. 7A, the number of tachyzoites or bradyzoites per 100 PV-Cysts was counted at random, in three independent experiments. The y-axis depicts the number of parasites per/PV-cysts, and the x-axis depicts time in hours.
Figure 7B:
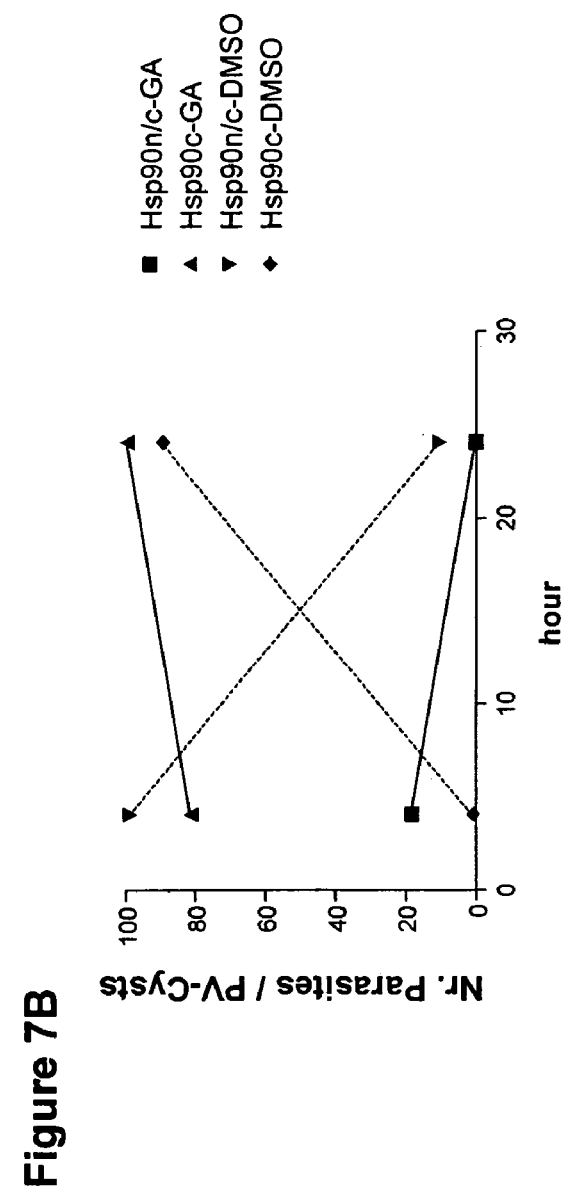
FIG. 7B shows the effect of GA on the Hsp90 subcellular localization. The y-axis depicts the number of parasites per/PV-cysts, and the x-axis depicts time in hours. Parasites with cytoplasmic Hsp90 were treated with GA (Hsp90c-GA) or DMSO (Hsp90c-DMSO); parasites with cytoplasmic and nuclear Hsp90 were treated with GA (Hsp90c,n-GA) or DMSO (Hsp90n,c-DMSO). 100 PV-Cysts were counted at random in three independent experiments.

In order to examine the effect of GA on bradyzoite to tachyzoite conversion, Me49 bradyzoites obtained from brain cysts of experimentally infected mice were incubated for 2 hours with GA, washed to eliminate the drug, and inoculated onto host cell cultures under tachyzoite conditions. The Hsp90 staining was monitored by IFA, 4 and 24 hours post-inoculation, FIG. 7. At 4 hours post-infection, all parasites were still bradyzoites: more than 90% were P21 positive and SAG1 negative (FIG. 7A). At 24 hours, however, the DMSO control parasites developed into tachyzoites (20% P21 positive and 80% SAG1 positive), but the GA treated bradyzoites were not able to switch to the tachyzoites form: more that 90% remained P21 positive and less than 5% were SAG1 positive (FIG. 7A). Similar results were obtained when anti-P34 antibody was used as a bradyzoite marker. FIG. 7B shows the subcellular localization of Hsp90 in the presence or absence of GA. As can be seen in this figure, DMSO control parasites developed into tachyzoites in agreement with the Hsp90 staining pattern: at 24 hours post-inoculation less than 20% showed an Hsp90n,c and more than 80% an Hsp90c. The staining pattern of GA treated bradyzoites showed tachyzoite-like Hsp90 staining: 80% of the bradyzoites showed an Hsp90c staining and only 20% showed an Hsp90n,c staining pattern. 100% of parasites exhibited Hsp90c 24 hours post-infection, suggesting that all of the were able to undergo the switch to the tachyzoite phenotype.

In addition, treated bradyzoites showed a reduced level of invasion (40-66% reduction) compared with DMSO treated parasites. Since invasion and replication were affected in GA treated parasites, the experiment carried out in FIG. 7 was repeated and a longer time course analyzed. At 72 hours, both GA treated and DMSO controls converted to tachyzoites and they were able to re-invade a new cell monolayer, indicating that the GA effect is reversible.

It was also discovered that Hsp90 is present in the cytosol of tachyzoites and both in the nucleus and cytosol of mature bradyzoites, establishing a strong correlation between the subcellular localization and these two developmental stages.

EQUIVALENTS

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

All references cited herein are incorporated in their entirety by reference.

What is claimed is:

1. A method for treating latent *Toxoplasma gondii* infection in a subject, comprising administering to the subject an effective amount of a heat shock protein 90 (Hsp90) inhibitor to treat the latent *Toxoplasma gondii* infection.

2. The method of claim 1, wherein the subject otherwise does not have a condition calling for administration of the Hsp90 inhibitor.

3. The method of claim 1, wherein the subject does not have a cancer.

4. The method of claim 1, wherein the subject does not have a cancer sensitive to the Hsp90 inhibitor.

5. The method of claim 1, wherein the Hsp90 inhibitor is geldanamycin A and the subject does not have a geldanamycin-sensitive cancer.

6. The method of claim 1, wherein the subject is immunocompromised or is at risk of becoming immunocompromised.

7. The method of claim 6, wherein the subject is infected with human immunodeficiency virus (HIV).

8. The method of claim 6, wherein the subject is receiving immunosuppressive therapy.

9. The method of claim 1, wherein the Hsp90 inhibitor is chosen from the group consisting of geldanamycin A (GA), 7-allylamino-1-deoxy-geldanamycin, 17-allylamino-17-demethoxy-geldanamycin (17-AAG), 17-dimethylaminoethylamino-geldanamycin (17DMAG), 17-(3-(4-maleimidobutyrcarboxamido)propylamino)-17-demethoxy-geldanamycin (17-GMB-APA-GA), Herbimycin A, Radicicol (RA), Novobiocin, Cisplatin, PU3, and PU24FC1.

10. The method of claim 1, wherein the Hsp90 inhibitor is chosen from the group consisting of geldanamycin A (GA), 7-allylamino-1-deoxy-geldanamycin, 17-allylamino-17-demethoxy-geldanamycin (17-AAG), 17-dimethylaminoethylamino-geldanamycin (17DMAG), and 17-(3-(4-maleimidobutyrcarboxamido)propylamino)-17-demethoxy-geldanamycin (17-GMB-APA-GA).

11. The method of claim 1, wherein the Hsp90 inhibitor is geldanamycin A (GA).

* * * * *

SEQUENCE LISTING

```
<160> NUMBER OF SEQ ID NOS: 9

<210> SEQ ID NO 1
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 1
cgacggtggg gtccaaat                                                 18

<210> SEQ ID NO 2
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 2
gagctcttct gcctggaa                                                 18

<210> SEQ ID NO 3
<211> LENGTH: 18
<212> TYPE: DNA
<213> ORGANISM: Artificial sequence
<220> FEATURE:
<223> OTHER INFORMATION: Synthetic oligonucleotide
```

<400> SEQUENCE: 3
ttggtcactt ccgagtac                                                      18

<210> SEQ ID NO 4
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 4
atcttcctcg gcgcggcaa                                                     19

<210> SEQ ID NO 5
<211> LENGTH: 10
<212> TYPE: PRT
<213> ORGANISM: T. gondii

<400> SEQUENCE: 5

Tyr Ser Asn Lys Glu Ile Phe Leu Arg Glu
1               5                   10

<210> SEQ ID NO 6
<211> LENGTH: 17
<212> TYPE: PRT
<213> ORGANISM: T. gondii

<400> SEQUENCE: 6

Lys Lys Glu Glu Gly Ala Glu Lys Lys Lys Thr Lys Lys Val Lys
1               5                   10                  15

Glu

<210> SEQ ID NO 7
<211> LENGTH: 17
<212> TYPE: PRT
<213> ORGANISM: T. gondii

<400> SEQUENCE: 7

Lys Lys Gly Leu Glu Leu Glu Asp Asp Glu Glu Glu Lys Lys Lys Phe
1               5                   10                  15

Glu

<210> SEQ ID NO 8
<211> LENGTH: 5
<212> TYPE: PRT
<213> ORGANISM: T. gondii

<400> SEQUENCE: 8

Met Glu Glu Val Asp
1               5

<210> SEQ ID NO 9
<211> LENGTH: 4
<212> TYPE: PRT
<213> ORGANISM: T. gondii

<400> SEQUENCE: 9

Arg Lys Lys Arg
1